(12) United States Patent
Fleisher

(10) Patent No.: US 8,345,918 B2
(45) Date of Patent: Jan. 1, 2013

(54) ACTIVE SUBJECT PRIVACY IMAGING

(75) Inventor: Michael Fleisher, Sunnyvale, CA (US)

(73) Assignee: L-3 Communications Corporation, New York, NY (US)

( * ) Notice: Subject to any disclaimer, the term of this patent is extended or adjusted under 35 U.S.C. 154(b) by 1689 days.

(21) Appl. No.: 10/987,426

(22) Filed: Nov. 12, 2004

(65) Prior Publication Data
US 2005/0232487 A1  Oct. 20, 2005

Related U.S. Application Data

(63) Continuation-in-part of application No. 10/824,875, filed on Apr. 14, 2004, now Pat. No. 7,123,185.

(51) Int. Cl.
*G06K 9/00* (2006.01)
(52) U.S. Cl. .......................... 382/103; 342/22
(58) Field of Classification Search .................. 382/103; 342/22; 348/143
See application file for complete search history.

(56) References Cited

U.S. PATENT DOCUMENTS

| | | |
|---|---|---|
| 4,866,424 A | 9/1989 | Parks |
| 4,901,084 A | 2/1990 | Huguenin et al. |
| 4,910,523 A | 3/1990 | Huguenin et al. |
| 4,940,986 A | 7/1990 | Huguenin |
| 5,047,783 A | 9/1991 | Hugenin |
| 5,073,782 A | 12/1991 | Huguenin et al. |
| 5,170,169 A | 12/1992 | Stephan |
| 5,181,234 A | 1/1993 | Smith |
| 5,202,692 A | 4/1993 | Huguenin et al. |
| 5,227,800 A | 7/1993 | Huguenin et al. |
| 5,367,552 A | 11/1994 | Peschmann |
| 5,455,590 A | 10/1995 | Collins et al. |
| 5,557,283 A * | 9/1996 | Sheen et al. ................... 342/179 |
| 5,600,303 A | 2/1997 | Husseiny et al. |
| 5,629,752 A * | 5/1997 | Kinjo .............................. 355/35 |
| 5,760,397 A | 6/1998 | Huguenin et al. |
| 5,781,650 A * | 7/1998 | Lobo et al. ..................... 382/118 |
| 5,805,098 A | 9/1998 | McCorkle |

(Continued)

FOREIGN PATENT DOCUMENTS
EP    1014471    6/2000

OTHER PUBLICATIONS

Park, Sung Cheol, Park, Min Kyu and Kang, Moon Gi, *Super-Resolution Image Reconstruction: A Technical Overview*, IEEE Signal Processing Magazine, vol. 20, No. 3, pp. 21-36, May 2003.

(Continued)

*Primary Examiner* — John Strege
(74) *Attorney, Agent, or Firm* — Kolisch Hartwell, P.C.

(57) ABSTRACT

A method of surveilling a subject including a person's body may include or an imaging system may provide interrogating the subject with electromagnetic radiation, and generating, from the interrogating, image data representative of at least a first image of at least a portion of the person's body. In some examples, a first portion of the body may be identified, and a first feature of the image may be determined based at least partially on the identified portion of the body. In some examples, the orientation of the person's body may be determined from one or more features of one or more image portions. In some examples, a portion of the image of the person's body may be replaced with a substitute image portion that may be a modified portion of the first image.

39 Claims, 11 Drawing Sheets

U.S. PATENT DOCUMENTS

| | | | |
|---|---|---|---|
| 5,835,616 A * | 11/1998 | Lobo et al. | 382/118 |
| 5,859,609 A * | 1/1999 | Sheen et al. | 342/179 |
| 5,956,525 A * | 9/1999 | Minsky | 396/3 |
| 6,057,761 A | 5/2000 | Yukl | |
| 6,072,494 A * | 6/2000 | Nguyen | 715/863 |
| 6,078,047 A | 6/2000 | Mittleman et al. | |
| 6,088,423 A | 7/2000 | Krug et al. | |
| 6,094,472 A | 7/2000 | Smith | |
| 6,184,926 B1 * | 2/2001 | Khosravi et al. | 348/239 |
| 6,215,890 B1 * | 4/2001 | Matsuo et al. | 382/103 |
| 6,342,696 B1 | 1/2002 | Chadwick | |
| 6,469,624 B1 | 10/2002 | Whan et al. | |
| 6,507,309 B2 * | 1/2003 | McMakin et al. | 342/22 |
| 6,518,915 B2 * | 2/2003 | Schutz et al. | 342/28 |
| 6,545,706 B1 * | 4/2003 | Edwards et al. | 348/169 |
| 6,665,373 B1 * | 12/2003 | Kotowski et al. | 378/90 |
| 6,697,503 B2 * | 2/2004 | Matsuo et al. | 382/118 |
| 6,703,964 B2 * | 3/2004 | McMakin et al. | 342/22 |
| 6,738,066 B1 * | 5/2004 | Nguyen | 345/474 |
| 6,738,507 B2 * | 5/2004 | Liasi et al. | 382/152 |
| 6,788,809 B1 | 9/2004 | Grzeszczuk | |
| 6,791,487 B1 | 9/2004 | Singh et al. | |
| 6,819,783 B2 * | 11/2004 | Goldberg et al. | 382/115 |
| 6,876,322 B2 * | 4/2005 | Keller | 342/22 |
| 6,901,163 B1 | 5/2005 | Pearce et al. | |
| 6,909,455 B1 * | 6/2005 | Edwards et al. | 348/169 |
| 6,927,691 B2 | 8/2005 | Yukl | |
| 6,937,182 B2 | 8/2005 | Lovberg et al. | |
| 6,965,340 B1 | 11/2005 | Baharav et al. | |
| 6,972,714 B1 | 12/2005 | Baharav et al. | |
| 6,972,775 B1 * | 12/2005 | Haakonsen | 345/646 |
| 7,076,102 B2 * | 7/2006 | Lin et al. | 382/218 |
| 7,088,851 B2 * | 8/2006 | Shinbata | 382/132 |
| 7,110,572 B1 * | 9/2006 | Benn | 382/110 |
| 7,180,441 B2 * | 2/2007 | Rowe et al. | 342/22 |
| 7,183,963 B2 | 2/2007 | Lee et al. | |
| 7,253,766 B2 * | 8/2007 | Foote et al. | 342/22 |
| 7,274,800 B2 * | 9/2007 | Nefian et al. | 382/103 |
| 7,280,068 B2 | 10/2007 | Lee et al. | |
| 7,283,085 B2 | 10/2007 | Lee et al. | |
| 7,298,318 B2 | 11/2007 | Baharav et al. | |
| 7,327,304 B2 | 2/2008 | Baharav et al. | |
| 7,333,055 B2 | 2/2008 | Baharav et al. | |
| 2001/0002932 A1 * | 6/2001 | Matsuo et al. | 382/118 |
| 2002/0041327 A1 * | 4/2002 | Hildreth et al. | 348/42 |
| 2003/0035001 A1 * | 2/2003 | Van Geest et al. | 345/753 |
| 2003/0086525 A1 * | 5/2003 | Rhee et al. | 378/63 |
| 2003/0091239 A1 * | 5/2003 | Imagawa et al. | 382/232 |
| 2003/0113018 A1 * | 6/2003 | Nefian et al. | 382/181 |
| 2003/0118216 A1 | 6/2003 | Goldberg | |
| 2003/0128150 A1 | 7/2003 | McMakin et al. | |
| 2003/0156199 A1 | 8/2003 | Shindo et al. | |
| 2003/0231788 A1 | 12/2003 | Yukhin et al. | |
| 2004/0080448 A1 * | 4/2004 | Lovberg et al. | 342/22 |
| 2004/0081338 A1 * | 4/2004 | Takenaka | 382/118 |
| 2004/0090359 A1 | 5/2004 | McMakin et al. | |
| 2004/0119716 A1 * | 6/2004 | Park et al. | 345/473 |
| 2004/0140924 A1 * | 7/2004 | Keller et al. | 342/22 |
| 2004/0263379 A1 * | 12/2004 | Keller | 342/22 |
| 2005/0030219 A1 | 2/2005 | Friedrich et al. | |
| 2005/0031166 A1 * | 2/2005 | Fujimura et al. | 382/103 |
| 2005/0093858 A1 * | 5/2005 | Tsai et al. | 345/419 |
| 2005/0110672 A1 * | 5/2005 | Cardiasmenos et al. | 342/27 |
| 2005/0147304 A1 * | 7/2005 | Nagahashi et al. | 382/190 |
| 2005/0152579 A1 * | 7/2005 | Park et al. | 382/103 |
| 2005/0185054 A1 * | 8/2005 | Edwards et al. | 348/169 |
| 2005/0196044 A1 * | 9/2005 | Nagahashi et al. | 382/190 |
| 2006/0066469 A1 | 3/2006 | Foote et al. | |
| 2006/0262902 A1 * | 11/2006 | Wattenburg | 378/57 |
| 2007/0223829 A1 * | 9/2007 | Nakashima et al. | 382/254 |

OTHER PUBLICATIONS

Segall, C. Andrew, Molina, Rafael and Katsaggelos, Aggelos K, *High-Resolution Images From Low Resolution Compressed Video*, IEEE Signal Processing Magazine, vol. 20, No. 3, pp. 37-48, May 2003.

U.S. Appl. No. 10/301,552, filed Nov. 21, 2002, McMakin.

Rajan, Deepu, Chaudhuri, Subhasis and Joshi, Manjunath V., *Multi-Objective Super Resolution: Concepts and Examples*, IEEE Signal Processing Magazine, vol. 20, No. 3, pp. 49-61, May 2003.

Ng, Michael K. and Bose Nirmal K., *Mathematical Analysis of Super-Resolution Methodology*, IEEE Signal Processing Magazine, vol. 20, No. 3, pp. 62-74, May 2003.

Capel, David and Zisserman, Andrew, *Computer Vision Applied to Super Resolution*, IEEE Signal ' Processing Magazine, vol. 20, No. 3, pp. 75-102, May 2003.

Vollmerhausen, Richard H. and Driggers, Ronald G., *Dynamic Sampling, Resolution Enhancement, and Super Resolution*, Analysis of Sampled Imaging Systems, Chapter 6, pp. 125-138, 2002.

Laws, Kenneth I., *Goal-Directed Texture-Image Segmentation*, SPIE, vol. 548 Applications of Artificial Intelligence II, pp. 19-26, 1985.

Laws, Kenneth I., *Rapid Texture Identification*, SPIE, vol. 238 Image Processing for Missile Guidance, pp. 376-381, 1980.

International Preliminary Report on Patentability and Written Opinion of the International Searching Authority, dated Nov. 23, 2007, for the corresponding international application No. PCT/US2005/40881.

European Patent Office, "Supplementary European Search Report, application No. EP05858620.7," mailing date Feb. 26, 2009 (6 pages). This EP application corresponds to U.S. patent 7,368,150 (U.S. Appl. No. 10/987,409) which has the same inventor as this application, U.S. Appl. No. 10/987,426.

Paul E. Keller, et al., "Privacy Algorithm for Cylindrical Holographic Weapons Surveillance System," Security Technology, Proceedings of the IEEE 33rd Annual International Carnahan Conference (held in Madrid, Spain on Oct. 5-7, 1999); IEEE, Piscataway NJ 1999, pp. 177-181.

David M. Sheen et al, "Concealed explosive detection on personnel using a wideband holographic millimeter-wave imaging system," Signal Processing, Sensor Fusion, and Target Recognition V, SPIE vol. 2755 No. 1, pp. 503-513, Apr. 8, 1996.

U.S. Patent and Trademark Office, Sathyanaraya V. Perungavoor, examiner, "Non-Final Office Action" for U.S. Appl. No. 10/987,409, mailing date Nov. 14, 2007 (11 pages). The '409 application (now U.S. patent 7,368,150) has the same inventor as this '426 application.

World Intellectual Property Organization, "International Search Report and Written Opinion of the International Searching Authority," for PCT/US2005/041044, dated Sep. 24, 2007 (11 pages). This PCT application corresponds to U.S. Appl. No. 10/987,409 (now U.S. patent 7,368,150) and has the same inventor as this '426 application.

Israel Patent Office, Office Action for Israeli Patent Application No. 183046 (corresponding to U.S. Appl. No. 10/987,409 having common disclosure and inventors with U.S. Appl. No. 10/987,426), including a letter from Sanford T. Colb & Co. dated Jun. 7, 2010 explaining the Office action, May 16, 2010, 9 pages.

European Patent Office, "First Examination Report, application No. EP05858620.7," mailing date Jun. 10, 2009 (1 page). This EP application corresponds to U.S. patent 7,368,150 (U.S. Appl. No. 10/987,409) which has the same inventor as this application, U.S. Appl. No. 10/987,426.

McMahon, Steve. "Softening, Blurring, Sharpening and Embossing Images." Mar. 7, 2003. Online: http://web.archive.org/web/20030307155319/http://www.vbaccelerator.com/home/VB/Code/vbMedia/Image_Processing/Blurring_Sharpening_and_Embossing/article.asp.

Keller, P.E., McMakin, D.L., Sheen, D.M., McKinnon, A.D., and Summet, J.W., "Privacy Algorithm for Cylindrical Holographic Weapons Surveillance System." Aerospace and Electronic Systems Magazine, IEEE. vol. 15, Issue 2. pp. 17-23. Feb. 2000.

McMillan, R.W., Currie, N. C., Ferris, D.D., Jr., and Wicks, M.D. "Concealed Weapon Detection using Microwave and Millimeter Wave Sensors". Microwave and Millimeter Wave Technology Proceedings, 1998. pp. 1-4.

Sheen, D.M., McMakin, D.L., and Hall, T.E., "Three-Dimensional Millimeter-Wave Imaging for Concealed Weapon Detection". IEEE Transactions on Microwave Theory and Techniques. vol. 49, Issue 9. pp. 1581-1592. May 2001.

* cited by examiner

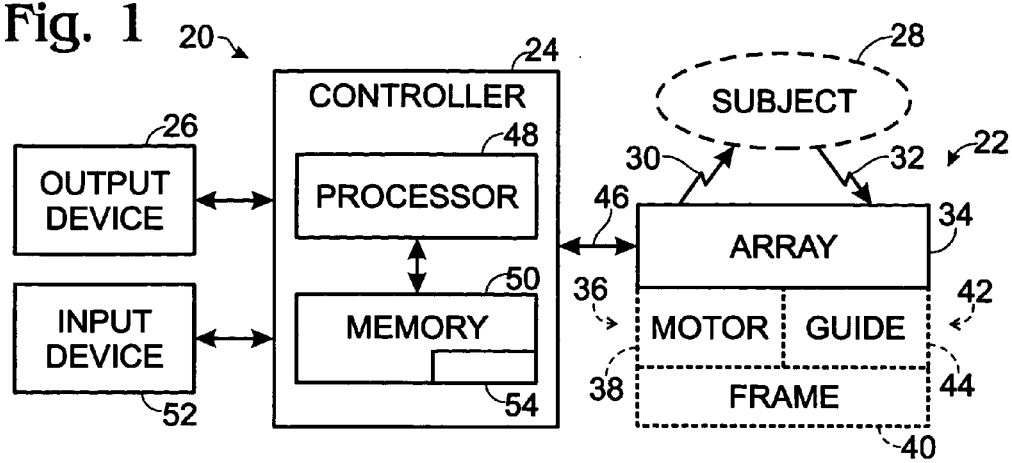
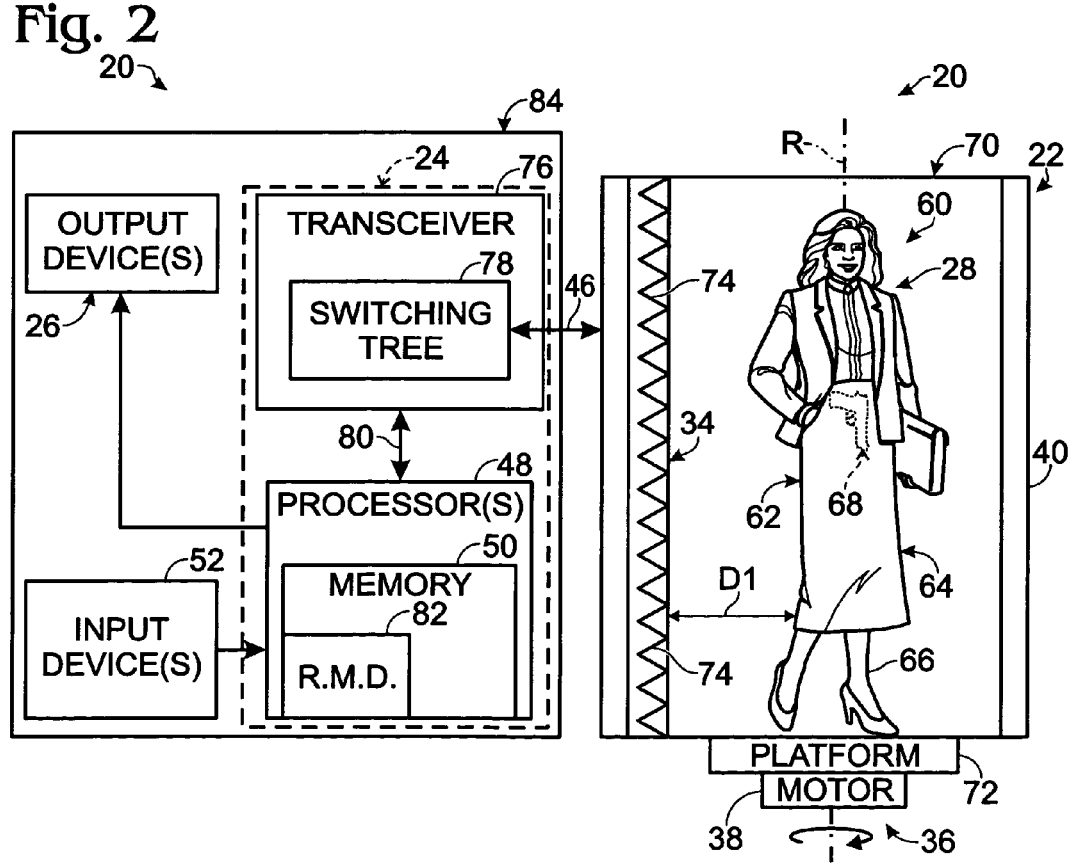

US 8,345,918 B2

ACTIVE SUBJECT PRIVACY IMAGING

RELATED APPLICATIONS

This application is a continuation-in-part of U.S. patent application Ser. No. 10/824,875 filed on Apr. 14, 2004, now U.S. Pat. No. 7,123,185, which application is incorporated herein by reference for all purposes. Also, this application is being filed with an application entitled ACTIVE SUBJECT IMAGING WITH BODY IDENTIFICATION by the same inventor.

BACKGROUND

Millimeter wave signals are used for radar and telecommunications. They are also capable of being used to generate data representative of a subject, by directing millimeter-wave signals at the subject and detecting the reflected signal. The data generated may then be used to produce an image of the subject. Examples of such imaging systems are described in U.S. Pat. Nos. 5,455,590; 5,557,283; 5,859,609; 6,507,309; and 6,703,964; U.S. patent application Ser. No. 10/607,552 filed Jun. 26, 2003; U.S. patent application Ser. No. 10/697,848 filed Oct. 30, 2003; and U.S. patent application Ser. No. 10/697,965 filed Oct. 30, 2003, which patent references are incorporated herein by reference.

BRIEF SUMMARY OF THE DISCLOSURE

A method of surveilling a subject including a person's body may include, or an imaging system may provide, interrogating the subject with electromagnetic radiation, and generating, from the interrogating, image data representative of at least a first image of at least a portion of the person's body. In some examples, a first portion of the body may be identified, and a first feature of the image may be determined based at least partially on the identified portion of the body. In some examples, the orientation of the person's body may be determined from one or more features of one or more image portions. In some examples, a portion of the image of the person's body may be replaced with a substitute image portion. Also in some examples, image data corresponding to at least a portion of the first image may be modified by replacing a first value of a given feature of each of at least a portion of the picture elements with a second value determined from the first values of the given feature of picture elements in a group of picture elements.

BRIEF DESCRIPTION OF THE SEVERAL FIGURES

FIG. 1 is a general diagram showing a surveillance imaging system.

FIG. 2 is a general diagram showing an example of an imaging system according to FIG. 1.

DETAILED DESCRIPTION OF VARIOUS EMBODIMENTS

Figure 3:
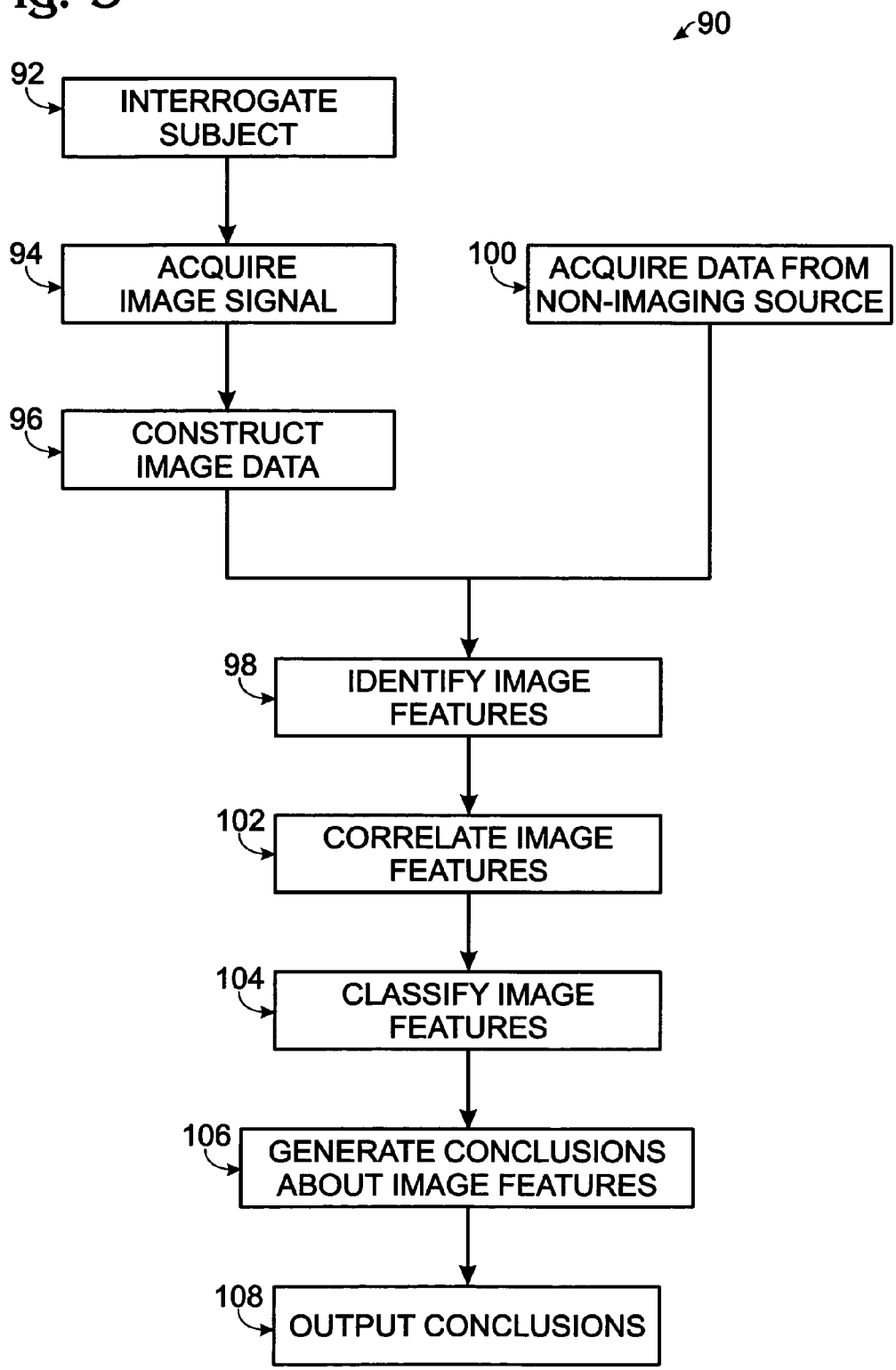
FIG. 3 is a general flow chart illustrating an example of a method of operation of an imaging system of FIG. 1 or FIG. 2.

There are situations in which it is desirable to identify features of a subject, particularly features of a person and any objects carried by the person. For example, it may be desired to determine whether the subject includes objects not apparent from a visual inspection of the subject. For example, when monitoring people prior to entry into a controlled-access environment, such as a public, private or government facility, building or vehicle, the accuracy of observation may be benefited by employing millimeter-wave imaging technology.

Regardless of the application, the benefits derived from the monitoring may depend on the speed and accuracy of the monitoring, and where appropriate, the effectiveness of identifying visually hidden objects. The detection of the location of parts of the person's body, such as the head, one or both legs, a privacy sensitive area, or other features, may assist in processing images of a subject, such as identifying objects or modifying an image to protect privacy concerns.

In the description and claims that follow, the terms "feature" and "characteristic" may be synonymous or related. For example, intensity, color, depth or distance relative to a reference, and values of intensity, color or depth may be considered to be features or characteristics of an image or picture element of an image. Further, one may be an aspect of the other. For example, image intensity may be a feature, and darkness, lightness, and variation may be characteristics of the intensity.

Shown generally at 20 in FIG. 1 is an exemplary imaging system. System 20 may include an interrogating apparatus 22, a controller 24, and in some systems, an output device 26. The system may interrogate a subject 28 in the sense that the interrogating apparatus transmits electromagnetic radiation 30 toward the subject, and in response, the subject emits or reflects electromagnetic radiation 32 that is detected by the interrogating apparatus. Optionally, interrogating apparatus may include physically and/or functionally separate or combined apparatus that collectively provide physical, electronic and/or virtual electromagnetic radiation and detection of radiation emitted from a subject.

Subject 28 may include all that is presented for interrogation by an interrogation system, whether human, animal, or inanimate object. For example, if a person is presented for interrogation, subject 28 may include the entire person's body or a specific portion or portions of the person's body. Optionally, subject 28 may include one or more persons, animals, objects, or a combination of these.

System 20 may be adapted to interrogate subject 28 by irradiating it with electromagnetic radiation, and detecting the reflected radiation. Electromagnetic radiation may be selected from an appropriate frequency range, such as in the range of about 100 megahertz (MHz) to 2 terahertz (THz), which range may be generally referred to herein as millimeter-wave radiation. Accordingly, imaging, or the production of images from the detected radiation, may be obtained using electromagnetic radiation in the frequency range of one gigahertz (GHz) to about 300 GHz. Radiation in the range of about 5 GHz to about 110 GHz may also be used to produce acceptable images. Some imaging systems use radiation in the range of 24 GHz to 30 GHz. Such radiation may be either at a fixed frequency or over a range or set of frequencies using one or more of several modulation types, e.g. chirp, pseudorandom frequency hop, pulsed, frequency modulated continuous wave (FMCW), or continuous wave (CW).

Certain natural and synthetic fibers may be transparent or semi-transparent to radiation of such frequencies and wavelengths, permitting the detection and/or imaging of surfaces positioned beneath such materials. For example, when the subject of interrogation is an individual having portions of the body covered by clothing or other covering materials, such as a cast, wound dressings, bandages, or the like, information about portions of the subject's body covered by such materials can be obtained with system 20, as well as those portions that are not covered. Further, information relative to objects carried or supported by, or otherwise with a person beneath clothing can be provided with system 20 for metal and non-metal object compositions, such as those used for prosthetic devices and the like.

Many variations of interrogating apparatus 22 are possible. For example, the interrogating apparatus may include any suitable combination, configuration and arrangement of transmitting and/or receiving antennae that provides interrogation of a subject, such as an array 34 of one or more antenna units, each of which may further include a single antenna that transmits and receives radiation, a plurality of antennae that collectively transmit and receive radiation, or separate transmitting and receiving antenna. Optionally, some embodiments may employ one or more antennae apparatus as described in U.S. patent application Ser. No. 10/728,456 filed Dec. 5, 2003, entitled "Millimeter-Wave Active Imaging System", the disclosure of which is incorporated herein by reference.

Depending on the interrogating apparatus, an imaging system may include an apparatus moving mechanism 36, represented by a motor 38, which may move interrogating apparatus 22 relative to a subject 28, may move one or more of a subject, one or more transmitting antennae, one or more receiving antennae, or a combination of these. Each motion mechanism 36 may be mounted relative to a frame 40 for moving the apparatus along a path defined by a movement control mechanism 42, such as a guide 44, including any associated motor indexers, encoders or other controls, as appropriate. The motion mechanism may be any appropriate mechanism that moves the interrogating apparatus, a part of the interrogating apparatus, and/or a subject, and may include a servomotor, stepper motor, or other suitable device.

Interrogating apparatus 22 may be coupled to controller 24. As contemplated herein, the controller may include structure and functions appropriate for generating, routing, processing, transmitting and receiving millimeter-wave signals to and from the interrogating apparatus. The controller, in this comprehensive sense, may include multiplexed switching among individual components of the interrogating apparatus, transmit and receive electronics, and mechanical, optical, electronic, and logic units. The controller thus may send to and receive from the interrogating apparatus signals 46, which may include appropriate signals, such as control signals and data signals.

Controller 24 may control operation of motor 38, and coordinate the operation of interrogating apparatus 22 with movement any of the interrogating apparatus or portions of the interrogating apparatus. Controller 24 may include hardware, software, firmware, or a combination of these, and may be included in a computer, computer server, or other microprocessor-based system capable of performing a sequence of logic operations. In addition, processing may be distributed with individual portions being implemented in separate system components.

Accordingly, controller 24 may include a processor 48 and a memory 50. Controller components such as output devices, processors, memories and memory devices, and other components, may be wholly or partly co-resident in interrogation apparatus 22 or be wholly or partly located remotely from the interrogation apparatus.

Processor 48 may process data signals received from the interrogating apparatus. The processor thus may include hardware, software, firmware, or a combination of these, and may be included in a computer, computer server, or other microprocessor-based system capable of performing a sequence of logic operations. The processor may be any analog or digital computational device, or combination of devices, such as a computer(s), microprocessor(s), or other logic unit(s) adapted to control interrogating a subject and receiving data signals 46, and to generate image data representative of at least a portion of the subject interrogated.

The description that follows is presented largely in terms of display images, algorithms, and symbolic representations of operation of data bits stored within a computer memory. Software, firmware, and hardware encompassing such representations may be configured many different ways, and may be aggregated into a single processor and program with unclear boundaries.

An algorithm is generally considered to be a self-consistent sequence of steps leading to a desired result. These steps require physical manipulations of physical quantities. Usually, though not necessarily, these quantities take the form of electrical or magnetic signals capable of being stored, transferred, combined, compared, and otherwise manipulated. When stored, they can be stored, transferred, combined, compared, and otherwise manipulated. When stored, they may be stored in any computer-readable medium. As a convention, these signals may be referred to as bits, values, elements, symbols, characters, images, terms, numbers, or the like. These and similar terms may be associated with appropriate physical quantities and are convenient labels applied to these quantities.

In the present case, the operations may include machine operations that may be performed automatically and/or in conjunction with a human operator. Useful machines for performing the operations disclosed include general-purpose digital computers, microprocessors, or other similar devices. The present disclosure also relates to apparatus for performing these operations. This apparatus may be specially constructed for the required purposes or it may comprise a general-purpose computer selectively activated or reconfigured by a computer program stored in the computer or other apparatus. In particular, various general-purpose machines may be used with programs in accordance with the teachings herein, or it may prove more convenient to construct more specialized apparatus to perform the required method steps.

A program or programs embodying the disclosed methods need not reside in a single memory, or even a single machine. Various portions, modules or features of them can reside in separate memories, or even separate machines. The separate machines may be connected directly, or through a network, such as a local access network (LAN), or a global network, such as what is presently generally known as the Internet. Similarly, the machines need not be collocated with each other.

Image data may include any data or data sets derived from an interrogation of a subject or relating to or associated with a past, present or future subject, whether processed, partially processed or unprocessed, or sub-sets of data, such as data for a portion of a subject; data that is manipulated in order to identify information corresponding to one or more given features of a subject; data that is manipulated or processed in order to present, for viewing by an operator or by another processor, information corresponding to one or more given features of a subject; or measurements or other information relating to a subject that is derived from received signals. Image data may be output to one or more output devices 26 coupled to processor 48, such as a storage device, communication link, such as a network hub, another computer or server, a printer, or directly to a display device, such as a video monitor. Processor 48 may also be coupled to an input device 52 such as a keyboard, cursor controller, touchscreen display, another processor, a network, or other device, communication link, such as a source of information for operating the system or supplemental information relating to a given subject.

In some embodiments, processor 48 may be coupled to memory 50 for storing data, such as one or more data sets generated by processor 48, or operating instructions, such as instructions for processing data. Memory 50 may be a single device or a combination of devices, and may be local to the processor or remote from it and accessible on a communication link or network. Operating instructions or code 54 may be stored in memory 50, and may be embodied as hardware, firmware, or software.

Data generated by the processor may thus be sent to and retrieved from memory 50 for storage. In some examples, data generated from interrogating a given subject may be retrieved for further processing, such as identifying information corresponding to a feature of the subject, for modifying image data, or for generating an image of a subject or portion of a subject derived from received signals. In such examples, the processor may be configured to identify or compare information corresponding to the features, such as identification of body portions, body orientation, or body features. In some examples, one or more data sets generated from interrogating a given subject at a given time may be stored in memory 48, and then may be compared with one or more data sets generated from interrogating the subject at a later time, such as sequential scans when a person's body is in different orientations. In some examples, the processor may be configured to identify information in multiple data sets, each generated at a different time, but corresponding to the same given feature of the subject, to compare the information corresponding to the feature at different times, and to compare the information for different portions of the person's body.

An imaging system, such as that illustrated in FIG. 1, may be used for interrogating in a variety of applications in which the controller may be configured to identify information in one or more data sets corresponding to one or more features of a subject. A second example of an imaging system 20 is illustrated in FIG. 2. In imaging system 20, a subject 28 in a subject position 60 may include a person 62 presented for interrogation by system 20. Person 62 is shown wearing clothing 64 over her or his body 66, which clothing conceals an object 68, shown in the form of a weapon. Subject 28 may be positioned in an interrogation station or portal 70 of system 20. Portal 70 may be configured in various ways for placement at a security checkpoint where it is desired to detect objects, such as weapons or contraband, on the person. Portal 70 may include, for example, a platform 72 connected to motion mechanism 36 in the form of motor 38. Platform 72 may be arranged to support subject 28. Motor 38 may be arranged to selectively rotate the platform about rotational axis R while subject 28 is positioned thereon. For the configuration shown, axis R may be vertical, and subject 28 may be in a generally central subject position 60 relative to axis R and platform 72.

Interrogating apparatus 22 may include an antenna apparatus 74 including a primary multiple-element sensing array 34. The interrogating apparatus 22 may include a frame 40 on which array 34 is supported. Array 34 may extend the full height of frame 40. Motor 38 may cause platform 72, and subject 28 to rotate about axis R. As a result, array 34 circumscribes a generally circular pathway about axis R. The antenna array may be about 0.5 to about 2 meters from radius R.

Antenna array 34 may include a number of linearly arranged elements 74 only a few of which are schematically illustrated. Each element 74 may be dedicated to transmission or reception of radiation or both, and the elements may be arranged in two generally vertical columns, with one column dedicated to transmission, and the other to reception. The number and spacing of the elements corresponds to the wavelengths used and the resolution desired. A range of 200 to about 600 elements can span a vertical length of about two or two and one-half meters.

Various other configurations for portal 70 and interrogating apparatus 22 may be used. For example, a two-dimensional transmit and receive array may be used, as well as an array that moves around a fixed subject platform, or an array that moves vertically and extends horizontally. Further, many variations of an antenna apparatus are possible. The antenna apparatus may include one or more antenna units, and each antenna unit may include one or more transmitting antennae and one or more receiving antennae. An antenna unit may include a plurality of antennae that may receive radiation in response to transmission by a single antenna. The antennae may be any appropriate type configured to transmit or receive electromagnetic radiation, such as a slot line, patch, endfire, waveguide, dipole, semiconductor, or laser. Antennae may both transmit and receive. The antenna units may have one or more individual antennae that transmit or receive like polarization or unlike polarized waveforms such as plane, elliptical, or circular polarization, and may have narrow or broad angular radiation beam patterns, depending on the application. Beam width may be relatively broad, i.e. 30 to 120 degrees for imaging applications that use holographic techniques, while narrow beam widths in the range of 0 to 30 degrees may be used for applications having a narrow field of view requirement.

Further, a single antenna may scan a subject by mechanically moving about the subject in a one- or two-dimensional path. A one- or two-dimensional array of antenna units may electronically and mechanically scan a subject. An imaging system may include one or a plurality of antenna apparatus. The antennae apparatus may be protected from the environment by suitable radome material, which may be part of the apparatus, or separate, depending on the mechanical motion that is required of the antennae apparatus or array. Examples of other array configurations are illustrated in copending patent application Ser. No. 10/728,456.

A controller 24 may control operation of interrogating apparatus 22. Controller 24 may include a transceiver 76 including a switching tree 78 configured to irradiate subject 28 with only one transmitting element 74 at a time, and simultaneously receive with one or more elements 74. Transceiver 76 may include logic to direct successive activation of each combination of transmit and receive antenna elements to provide a scan of a portion of a subject 28 along a vertical direction as platform 72 and the subject rotate.

An image signal 46 received from array 34 may be downshifted in frequency and converted into an appropriate format for processing. In one form, transceiver 76 may be of a bi-static heterodyne Frequency Modulated Continuous Wave (FM/CW) type like that described in U.S. Pat. No. 5,859,609. Other examples are described in U.S. Pat. Nos. 5,557,283 and 5,455,590. In other embodiments, a mixture of different transceiver and sensing element configurations with overlapping or nonoverlapping frequency ranges may be utilized, and may include one or more of the impulse type, monostable homodyne type, bi-static heterodyne type, and/or other appropriate type.

Transceiver 76 may provide image data 80 corresponding to the image signals to one or more processors 48. Processor 48 may include any suitable component for processing the image data, as appropriate. Processor 48 may be coupled to a memory 50 of an appropriate type and number. Memory 50 may include a removable memory device (R.M.D.) 82, such as a tape cartridge, floppy disk, CD-ROM, or the like, as well as other types of memory devices.

Controller 24 may be coupled to motor 38 or other drive element used to selectively control the rotation of platform 72. Controller 24 may be housed in a monitor and control station 84 that may also include one or more input devices 52, such as operator or network input devices, and one or more displays or other output devices 26.

A general flow chart 90, illustrating exemplary operation of surveillance system 20, is shown in FIG. 3. Two data acquisition phases are illustrated. Interrogating apparatus 22 interrogates a subject 28 at 92. Image information is detected during the interrogating and an image signal is generated. Processor 48 acquires the image signal at 94. The acquired image signal is then processed at 96 to construct image data. Image data is analyzed to identify image features at 98. As is explained further below, image features or characteristics derived from image data may be any identifiable aspect of the image data or associated image, such as the shape, configuration, arrangement, texture, location of one or more objects 68 relative to a person's body 66, or features of the person's body, such as orientation, position, texture, specific body parts, size, shape, configuration, symmetry, or other appropriate aspect.

One or more input devices 52 may be a source of image data, such as subject information, and may be separate from an interrogating apparatus, such as a data base with information on a particular person. The data from a supplemental source may be acquired at 100. A supplemental source also may be a sensor that detects general features of the subject 28, such as the general detection of a substance, a feature identifying the person 62, or context data stored in a memory relating to the subject Such supplemental image features may also be identified at 98. The existence of a substance, an identification of the person or a characteristic, class or categorization of the person, and other appropriate indicators or information may be features of the subject, in addition to features identified from the image data. Examples of features of the image data may include the location of features of the image that may correspond to an object or a specific part of the body, such as the head, legs, torso or the like, the characteristics of the body in a particular area, or the other appropriate features.

The various identified image features may then be correlated with each other at 102. For example, the identification of an object on the side of a person from an imaging apparatus may be correlated with the detection of metal in the middle zone of the person, a badge identifying the person, and context data previously stored in memory indicating that the person is a security guard and has high security clearance.

The identified or correlated features may then be classified at 104. Classification of features may be a logical process for determining the likelihood that detected features correspond to a suspect object or a false alarm. For example, the detection of various characteristics or certain combinations of characteristics in the same zone of an image may indicate that the image portion is an object. Further, given that the person is identified as a security guard, it is highly likely that the object is a gun. Also, the person may be authorized to carry a gun in this position as part of her duties. The object would thus be given a high weight of being a suspect object, but given a low weight as a security risk, due to the status of the person as a security guard.

Any set of corresponding features can be assigned a corresponding relative indicator, such as weight, value or attribute. An area of a subject may thus be assigned a high value even though no image object is detected. For example, a sheet of plastic explosive taped to a person's body may appear smoother than the rest of the person's body. The structure of an object also may be the basis of assigning a value, such as dimensions, shape and edge characteristics.

Once the image features are classified, then conclusions are generated at 106 about the combinations of image features. The conclusions may then be output at 108, as appropriate, such as via a display, report or alarm condition.

The remaining figures illustrate various exemplary procedures for identifying features of a subject from image data received by a processor, such as processor 48 receiving data from an interrogating apparatus 22. Generally, these images represent data. The steps described may be performed without actually producing a displayed image, or without producing data that provides visual characteristics suitable for display. Accordingly, many of the images presented are presented in visual form to facilitate an understanding of the associated processes, but formation or display of the associated data may be optional.

FIGS. 4-16 illustrate an example of a method for identifying a portion of a body of a subject. Generally, a method of surveilling may include interrogating a subject, including one or more persons and detectable objects, with electromagnetic radiation in a frequency range of about 100 MHz to about 2 THz; generating, from the interrogating, image data representative of at least a first image of at least a portion of the person's body; identifying from the image data at least a first portion of the body; and determining from the image data at least a first feature of the image based at least partially on the identified portion of the body.

Figure 4:
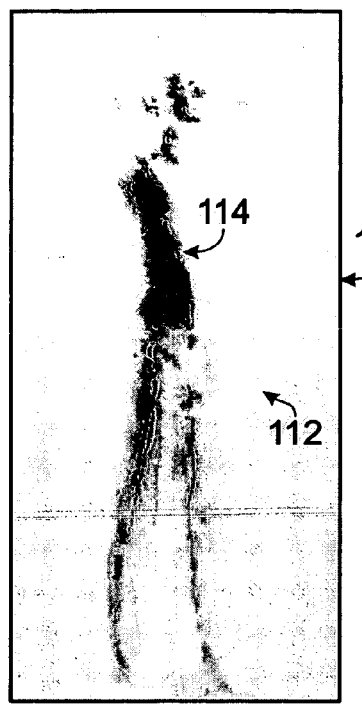
FIG. 4 is a reversed representative image of a subject from an imaging system of FIG. 1 or FIG. 2.

More particularly, these exemplary figures illustrate a method for identifying in an image the top of an interrogated person's head. The image may be formed by a matrix of picture elements, also referred to as pixels, or simply pels. As has been mentioned, these various images represent data. The steps described may be performed without actually producing a displayed image, or without producing data that provides visual characteristics suitable for display. The images in the figures are intended to facilitate an understanding of the processes described, and are not necessarily a part of the associated process. In FIG. 4, an image 110 of a subject 28 may distinguish between portions of the image that relate to the subject and portions of the image that relate to the background, including structure other than the subject. This distinction may be provided in an image by variation in a value of a feature, such as intensity, color and/or a topographical data, such as depth or distance from a reference.

Most of the graphical images included in the figures are shown in a reverse image in order to produce lighter images. Lighter images tend to be more readily reproduced using such duplicating equipment as printers, copiers and scanners. Thus, although images in which subjects are shown with lighter, and therefore brighter, intensities may be more readily and realistically perceived, it will be appreciated that the methods disclosed and discussed apply to either form of representation, or to any representation or valuation of data or characteristic that provides a distinction, whether or not suitable for display.

In the example shown in FIG. 4, image 110 includes a relatively light background 112 and a darker subject 114. Accordingly, in this representation format, the background generally has an intensity level above (lighter than) a threshold, and the subject generally has an intensity level below the threshold.

Due to the nature of interrogating apparatus 22, there may be inconsistencies or anomalies in portions of the image where the background has intensity levels similar to those of the subject, and the subject has intensity levels similar to the background. This image, representing the associated image data, may be analyzed to determine the location of the body or a body part, such as the top of the head. This analysis may include or be based in whole or in part on an analysis of any appropriate feature or features of the data, such as the intensity levels of the pixels. Determination of a selected aspect of the image to be determined may include one or more features.

Data represented by input image 110 may be used to determine a feature of the body, such as the location of a body part or region. However, improved reliability of the results may be provided by additional processing. As an example, an image may be morphed (transformed) by modifying the image based on features of the image. Morphing image data may be considered modifying or altering the image data by applying one or more morphological operators, such as operators described below and referred to as dilation, erosion, closing and opening.

Specific examples may include applying a specific transform kernel to the image pixels, or by processing pixels in an appropriate way, such as by modifying values based on pixel values in a window associated with a pixel. For example, a pixel value may be replaced by the lowest, highest, average or other value determined from pixels in an m×n window, such as a 7-pixel wide by 3-pixel high window, with the affected pixel located in the center of the window. Many variations of such a process are possible for producing morphed images with various corresponding characteristics. Further, a combination of such techniques may be used on the same image or image portion or on different portions of an image region.

As a result, a morphological operator that replaces pixel values with a dark value in a window of pixels, will tend to dilate dark features and erode light features. Conversely, a morphological operator that replaces pixel values with a light value in a window of pixels, will tend to erode dark features and dilate light features. As used in this description, then, the operator referred to as "opening" refers to first eroding light features (dilating dark features) followed by dilating light features (eroding dark features). The operator referred to as "closing" refers to first dilating light features (eroding dark features) followed by eroding light features (dilating dark features). Opening, then, tends to eliminate or reduce light spots and closing tends to eliminate or reduce dark spots. Additionally, opening and closing may be at least somewhat size-maintaining operators in that an initial change in size of an image feature may to some extent be corrected or compensated for by a reverse change in size.

Image 110 may be processed in a way that tends to eliminate image anomalies. For example, applying one or more appropriate morphological gray level operators, also referred to as openings, to the pixels forming image 110 may produce an image such as image 120 shown in FIG. 5. The pixels in image 120 may be derived from the pixels in image 110 in the following way. Initially, the value for each selected pixel in image 110 may be replaced with a value derived from a group of one or more pixels in the image, which group may include the selected pixel, and may be related in position to the selected pixel. For example, the group of pixels may be those pixels within a given distance of the selected pixel. This may be accomplished by considering the values of pixels in an m×n pixel window centered on or otherwise associated with the selected pixel, where m and n may be integers. A value based at least in part on the values of pixels in the group may be selected, such as a maximum value, a minimum value, an average value, or the like. Any suitable size of the window and function performed on the pixels in the window may be used. In this example, initially the minimum pixel value for the pixels in the window may be assigned to the selected pixel, resulting in eroding lighter image area.

The size of the window may be selected to fit a particular application, such as a particular imaging system, subject matter, or the like. For example, a window that is three pixels high vertically and nine pixels wide horizontally may be used to produce bands in the image that are horizontally elongate. The reason for this is that horizontal groups of pixels are affected more than vertical groups of pixels. If a pixel value is assigned that corresponds to a given range of values, then image features having pixels in that range of values will be increased in size, and associated features outside that range will be reduced. Thus, for example, where a subject in an image is dark and a background is light, as in FIG. 4, the subject may be dilated by selecting a dark or low value from pixels in each window, thus enlarging the subject and closing groups or stretches of lighter pixels that are small, such as holes, islands, or lines in the darker subject. Conversely, the subject may be eroded by selecting a light or high value from pixels in each window, thus reducing the size of the subject and opening small groups or stretches of lighter pixels in the darker subject. In this example, then, the effects realized depend on the window size and position relative to a selected pixel, as well as the value determined the values of pixels in the window. Different parameters may be used for each step of the process.

In one process referred to as closing, subject 114 may be eroded, making it smaller and lighter, and then dilated, making it larger, darker and smoother. The result of such a process is image 120 shown in FIG. 5. For image data that has not been reversed, in which case background 112 is dark and subject 114 is light, the operator of opening, with corresponding parameter values, such as window sizes and pixel values, would produce equivalent results. Image 120 may include a background 122 and a subject 124. If the window size is the same or nearly the same for both phases of this process, the resulting subject image may be about the same size as the original subject image.

Other image processing steps may be used. The image processing steps described may be reversed in order, only one step may be used, or additional steps may be used. Other criteria may be used for selecting a replacement pixel value, and not all pixel values need to be replaced or included in each step.

An imaging system 20 adapted to identify objects on a person's body may display identified objects on a monitor or other display device for observation by a system operator or other user. Some people may be concerned about a system that is capable of imaging the surveilled person's body, and in particular certain areas that may be referred to generally as privacy areas or regions. In order to avoid such issues, original images of objects may be displayed on an image of the surveiled person's body that is appropriately modified to avoid displaying the privacy areas. A privacy or other selected area of the original, detailed image of a person's body or portion of a person's body may be replaced with a substitute image, such as an image of the person's privacy area after being modified as described herein, or the entire image may be modified to provide an unclear image, such as image 120 shown in FIG. 5. Other examples of privacy imaging are also described in U.S. patent application Ser. No. 10/824,875 filed on Apr. 14, 2004.

Image 120 also may be analyzed directly and/or further processed to identify, in this case, the top of the head. This may include distinguishing between the subject and the background based on respective characteristics of each. Reliability, though, may be improved by applying a threshold to image 120 to produce a two-level image, such as image 130 shown in FIG. 6. All pixels below a given threshold may be assigned a given value for intensity or color, such as an extreme value corresponding to the value for black. In contrast, all pixels above the given threshold may be assigned a second given value, such as a value corresponding to white. Resulting image 130 includes a white background 132 and a black subject 134. There are relatively few black spots or islands in the background.

Further processing may be used to facilitate further analysis, such as to round out the bi-level image to make subject regions more continuous and eliminate smaller islands or stretches of black or white. This may be accomplished by further processing the image in a manner similar to the manner in which image 120 is produced. That is, the value of each pixel of a new image may be set equal to the lowest pixel value of those pixels in an m×n pixel window, such as a 3×3 pixel window. Such a processing also slightly enlarges (dilates) the dark subject. The subject may be reduced in size by repeating this process and using the highest pixel value instead of the lowest. A process reverse to this process may be used when image data corresponds to a light subject compared to the background.

Figure 7:
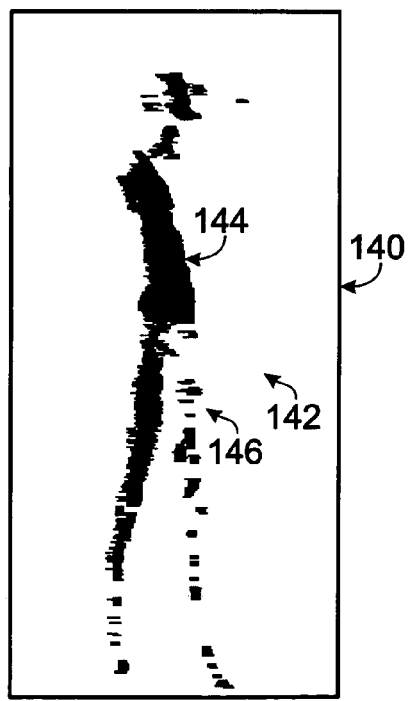
FIG. 7 is a yet further modified image derived from the image of FIG. 6.

One possible result is image 140, having a background 142 and a subject 144, shown in FIG. 7. It is seen that in the particular image processing applied, subject 144 appears to include vertical stacks of horizontally elongate pixel arrays or bands 146 resulting generally from applying an opening with horizontally elongated dimensions to the image. By applying certain criteria, such as is described below with reference to FIGS. 15 and 16, image 140 could be analyzed to determine automatically the location of a body part or region, such as the top of the head. However, it has been found that a body mask, such as image 140, that is derived or based at least in part on additional information, may produce more reliable results.

Figure 8:
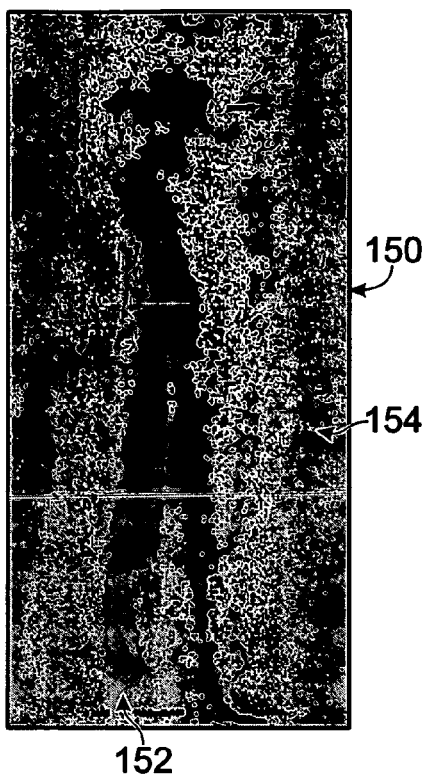
FIG. 8 is a reverse image corresponding to the image of FIG. 4 of relative detected distance of the subject from a reference.
Figure 9:
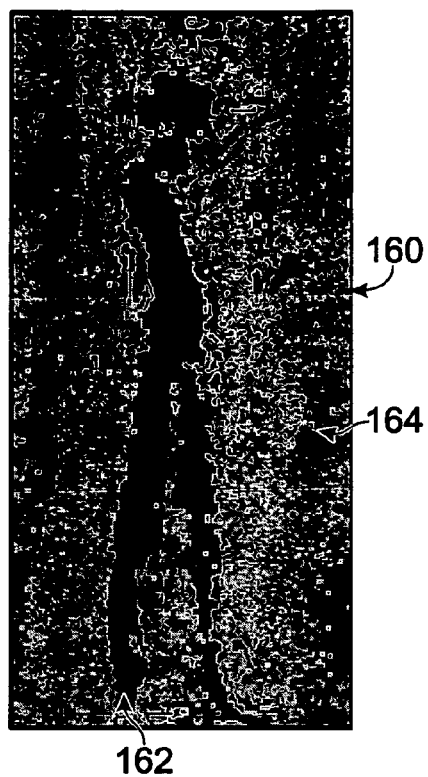
FIG. 9 is a modified image derived from the image of FIG. 8.

For example, FIG. 8 includes an image 150 of relative depths or distance values for pixels in image 110 from a reference, such as from a sensing array 34 shown in FIGS. 1 and 2. This image is of reverse intensity values, so the lighter the pixel, the shorter the distance to the reference. It is seen that the imaging system used may produce relatively consistent depth values for subject 152, with the person's right leg appearing closer and therefore lighter than the left leg. On the other hand, background area 154 may be generally mottled and inconsistent, indicating greater localized variance in depth values.

Image 150 may be further processed to further distinguish the subject from the background. One way that this may be done is by generating a new image 160 shown in FIG. 9 that represents the range or variance in depth in a region around each pixel of image 150. That is, for each pixel of image 150, a determination may be made of the variation in depth in a window, such as a 3-pixel by 3-pixel window. A selected low variation or threshold value may be assigned a first selected pixel intensity value, such as a minimum value corresponding to black. The threshold value may be no variation of depth or a selected range of depth in the window. A corresponding value may be assigned to the pixel indicative of the variation when a variation greater than the threshold variation is found. This may be a second value, such as a maximum or other distinctive value, or a representation of the actual value. Optionally, a second selected pixel intensity value may by assigned to the pixel when a range greater than the threshold value is identified. In this process, then, it may be necessary only to search the pixels in the window until a variance greater than the threshold variance is determined.

Image 160 represents one result of such a process. Image 160 includes a subject 162, indicated by the predominantly black regions where low depth variance was found. A background 164, having regions of increased depth variance, correspondingly is characterized by increased variance in the ranges of depth found.

Image 160 also may be processed to clearly identify those areas of lower variance from those areas characterized by higher variance. As mentioned, the regions of the minimum variance may be given a first selected value, and all other regions a second, distinctive selected value. However, portions of the subject may include regions with more depth variance than the minimum variance. In this case, a threshold variance value may be used, with pixels less than (or equal to) the threshold value assigned the first selected pixel value and pixels greater than (or equal to) the threshold value assigned the second selected value.

Figure 10:
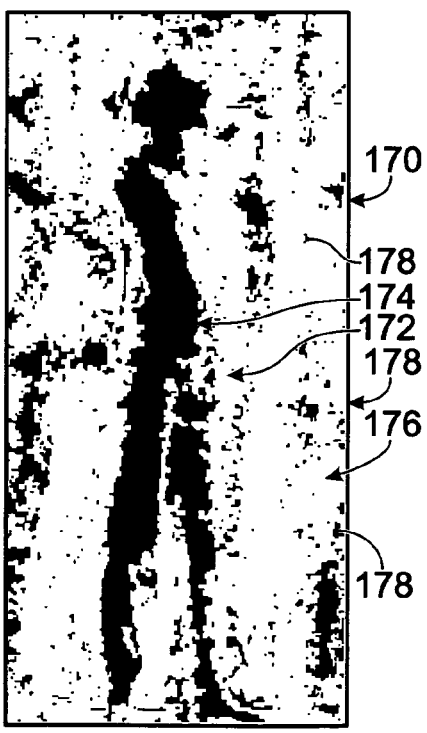
FIG. 10 is a further modified image derived from the image of FIG. 9.

FIG. 10 illustrates an image 170 in which regions 172 of lower depth variance have been assigned a value corresponding to black, which includes a subject 174. Correspondingly, the remaining regions 176 of higher depth variance, generally corresponding to the background, that were assigned a distinctive value, in this case, corresponding to white. Other values and representations may also be used. It is seen that there are numerous spots 178, also referred to as blobs or islands, throughout the image.

Figure 11:
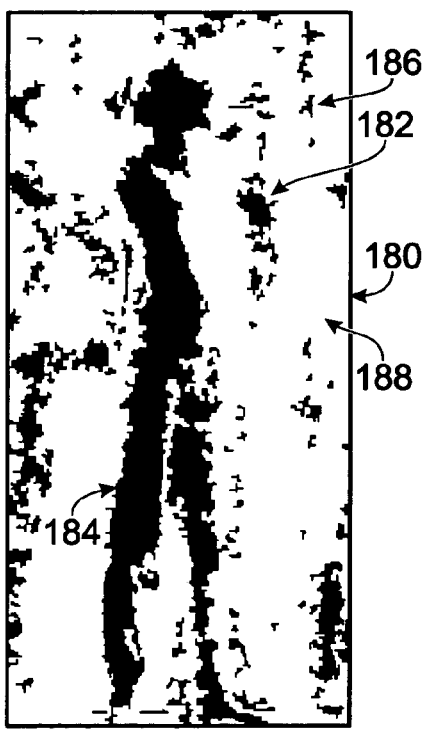
FIG. 11 is a yet further modified image derived from the image of FIG. 10.
Figure 12:
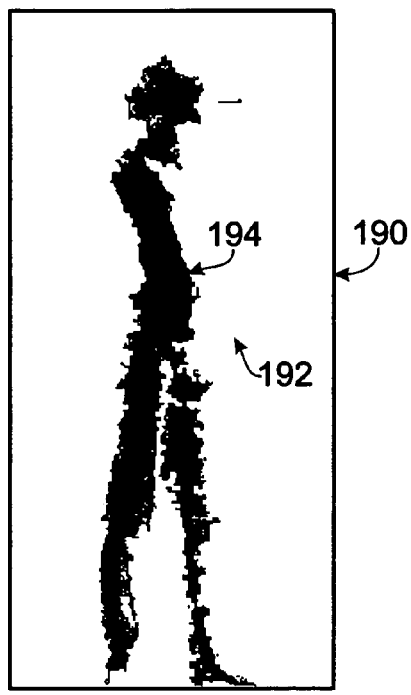
FIG. 12 is a body mask derived from the images of FIGS. 7 and 11.

Many spots 178 may be removed by processing image 170. Considering the generally continuous extent of subject 174, elimination of spots smaller than a selected threshold size may be removed. One way that this may be accomplished is to simply remove those spots of contiguous pixels of the same value. For this reversed image, the value selected corresponds to black. In order to define a spot, the notion of connectedness may be introduced. Two types of connectedness can be defined, four-connectedness or eight-connectedness. Two pixels are four-connected if they are vertically or horizontally adjacent. Two pixels are eight-connected if they are vertically, horizontally, or diagonally adjacent. Using the definition of connectedness that is selected, the size of a spot may be quantified as the number of connected pixels belonging to it. Two pixels belong to the same spot if and only if there is a path of connected pixels starting with one and ending with the other. An example of a modified image 180 after such a process is depicted in FIG. 11. Similar to image 170, image 180 includes black regions 182, including a subject 184 and remaining spots 186 on a white background 188. The number of smaller spots is substantially reduced.

Although the determination of body parts or regions may be identified from any one of the preceding images, improved reliability of results may be achieved by combining two or more of the images to form a composite image. For example, an image 190 depicted in FIG. 12 may be produced by combining images 140 of FIG. 7 with image 180. This may be done in various ways. For instance, new black regions may include all of the pixels that are black in one or both of the other images. Optionally, the other images may be used as a filter. For example, pixels may be identified or flagged if they are black in both images. The flagged pixels may then be assigned a distinctive value relative to a background 192, such as a value corresponding to black for a background that has a value corresponding to white. As a further filter, the flagged pixels may be assigned the distinctive value if one or more further conditions are met. For example, those flagged pixels may be selected if the intensity value of the pixel input image 110 is also below a threshold value. Image 190 depicts such an image, in which a subject 194 having pixels that meet the selected criterion is shown in black and the background 192 shown in white.

Image 190 may be used to determine one or more features of the subject or it may be processed yet further to provide a more reliable basis for defining the subject. One way to process the image further is to add to subject 194 of image 190 pixels of image 110 not included in subject 194 that have a selected intensity value or range of values, such as a value below a threshold value (since in image 140, subject 114 is characterized by and distinguished generally from background 112 by the darkness of the pixels). To particularly distinguish them from the background, pixel values may be selected that are, in this case, close to the minimum value.

Figure 13:
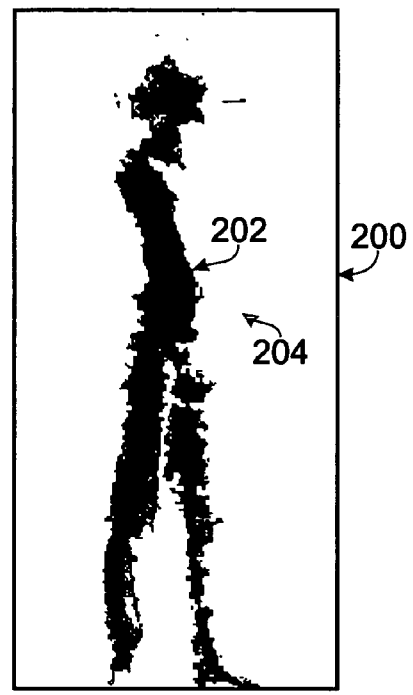
FIG. 13 is a modified image derived from the images of FIGS. 4 and 12.

An exemplary resulting image is image 200 shown in FIG. 13, including an enhanced subject 202 and background 204. It is seen that for the image depicted, the differences between images 190 and 200 are subtle, and include the addition of some small black spots.

As discussed above, further processing may be used to eliminate some or all of these spots. Additional steps of eroding and/or dilating image 200 may produce a final, "clean" image 210, also referred to as a body mask, shown in FIG. 14. Image 210, similarly, may include a subject 212 and a background 214. Image 210 may be well enough defined to allow reliable identification of a body part or portion based upon suitable criteria.

Figure 15:
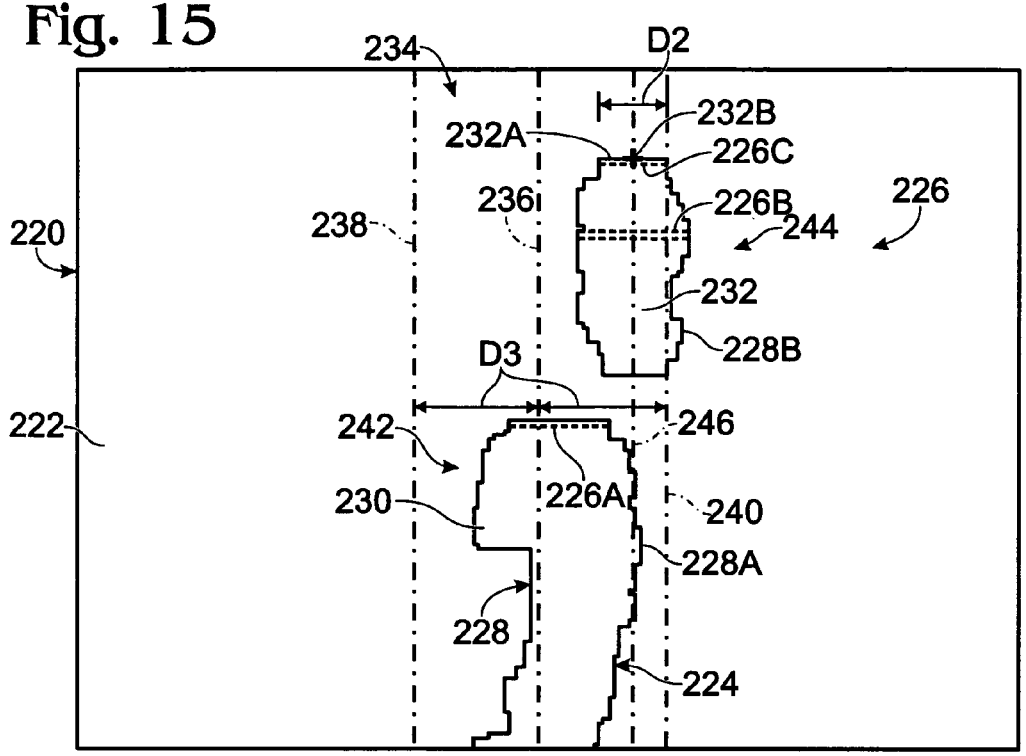
FIG. 15 is an illustration of features of a body mask derived from a different image.

An outline of an enlarged upper portion of an exemplary image 220, different than image 210 and in outline form, is illustrated in FIG. 15. Image 220 includes a background 222 and a subject 224 produced with a process similar to the process described with reference to FIGS. 4-7. Subject 224 may be thought of as being formed of a plurality of bands 226. The edge of subject 224 defines a boundary 228 between the subject and the background. In this image, subject 224 includes a torso 230 defined by a boundary 228A, and a head 232 defined by a boundary 228B.

Examples of bands 226 include a band 226A at the top of torso 230, band 226B in an intermediate portion of head 232, and band 226C at the top of the head. Bands 226 are seen to have different horizontal lengths. For example, bands 226A, 226B and 226C have different lengths. Band 226C is shown to have a length D2.

There may be one or more criteria used to determine the location of head 232, the location of the top 232A of the head, or even more particularly, the center 232B of the top of the head. Some images may have false or non-subject white areas in the background of image 220. Some of these may be eliminated or reduced by limiting consideration to a region 234 of the image. Region 234 may be reduced by limiting it to regions in which the head is known to occur.

One criterion may be that region 234 is limited horizontally to an intermediate portion of the image. For example, a band 226 may only be considered if at least a portion of it is within a certain distance from the horizontal center of the image, such as within 20 percent of the center of the image. In FIG. 15 the horizontal center of image 220 may be represented by vertical dash-dot line 236. Dash-dot lines 238 and 240 separated a distance D3 from line 236, may indicate lines that are each about 20 percent of the distance from the center to an outer edge. In an image that has a width of 180 pixels, for example, a band may be considered if at least a portion of it is within the center 40 pixels of the image, corresponding to a distance D3 equal to 20 pixels from the center. Other values may also be used. For instance, in some systems the distance D3 may correspond to ten, twenty-five, forty, fifty or other percent of the width of the image.

Another criterion might be that region 234 is limited to a vertically limited portion of image 220. For example, a portion of one or both of the upper and lower outer margins of the image may be ignored. Further, the portion considered may not be centered about the vertical center of the image. For instance, if it is known that significant anomalies may exist along the upper edge of the image and there may be a large variation in the heights of the subjects, only the bottom 90 percent of the image may be considered. Other portions may be appropriate, depending on the application.

Yet another criterion might be that a band 226 may be required to be of a particular size to be considered. For example, a band may be required to have a length within a certain range of lengths, such as less than a maximum number of pixels in length, more than a minimum number of pixels in length, or both. For instance, a band may only be considered if it is at least 8 pixels in length and/or not more than 50 pixels in length. This criterion may thereby omit smaller anomalies or body parts, such as an arm, as well as larger body parts, such as some of those for a torso.

In the example shown in FIG. 15, all three of bands 226A, 226B and 226C may satisfy these criteria, and therefore be considered in determining where the head is located. In order to further refine the search for the head, an additional criterion might require that the image around part or all of a considered band satisfy certain conditions. For example, a criterion may be that a band has other similar bands below it, and no band above it. Bands 226A and 226B would not satisfy this requirement, as there are other bands above them. Band 226C, though, satisfies this requirement, since there are bands below it, but none above it. Since this band also satisfies the other criteria discussed above, a conclusion can be made that band 226C represents the top 232A of the head.

In some applications, it may further be desired to identify the center 232B of the top of the head. A reasonable conclusion may be that the horizontal center of band 226C represents center 232B. Knowing the center of the top of the head, it may then be concluded that some other body parts, such as the torso and legs, are below the top of the head, when a person is interrogated in a standing position. Also, it may be concluded that subject 224 may be divided into first and second or left and right image subject sides 242 and 244 based on the location of the head, or more particularly, the center of the head. A vertical line, represented by dash-double-dot line 246, passing through head center 232B may separate sides 242 and 244.

Figure 16:
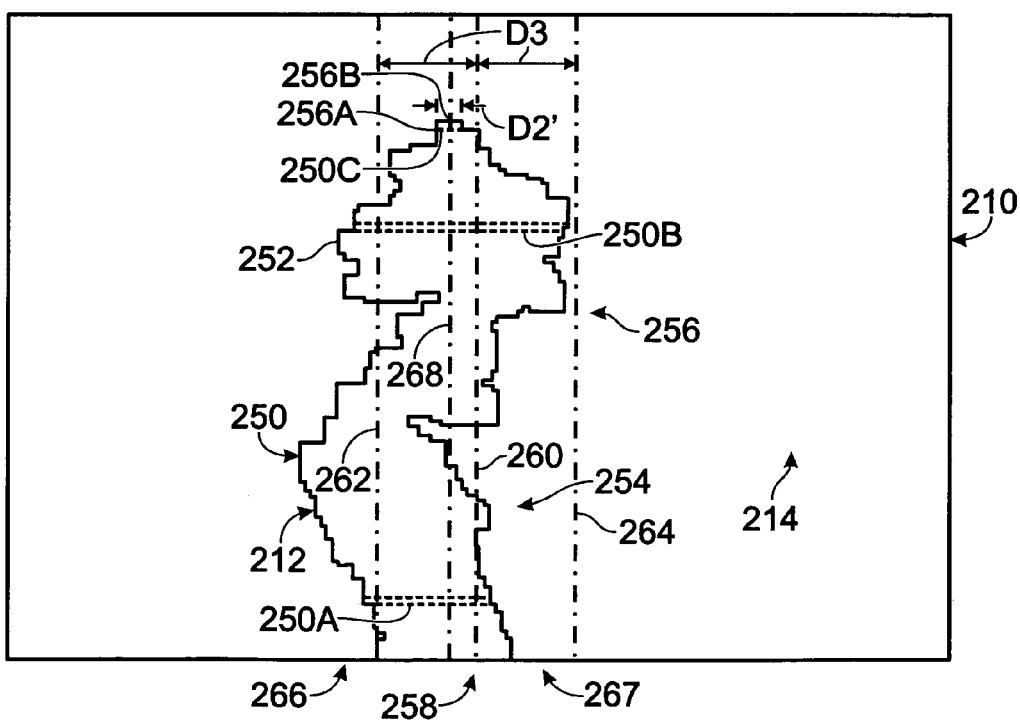
FIG. 16 is an illustration of features of the image of FIG. 14.

Criteria like the criteria applied to image 220 may also be applied to image 210 for identifying the location of a part or portion of the subject 212. An enlarged upper portion of the image is shown in FIG. 16 with the subject 212, formed of bands 250, and background 214 both shown in white and separated by an outline or boundary 252. In this image, the upper portion of subject 212 forms an uninterrupted region, including a torso 254 and a head 256. Examples of bands 250 include a band 250A in torso 254, band 250B in an intermediate portion of head 256, and band 250C at the top of the head. Bands 250 are seen to have different horizontal lengths. Band 250C is shown to have a length D2.

As discussed above, there may be one or more criteria used to determine the location of head 256, the location of the top 256A of the head, or even more particularly, the center 256B of the top of the head. A limited region 258 of consideration may be that region that is a horizontal distance D3 from a center line 260. The sides of such a region 258 may be represented by vertical dash-dot lines 262 and 264 separated a distance D3 from line 260, may indicate lines that are each about ten, twenty-five, forty, fifty percent of the width of the image, or other suitable portion of the image.

Applying other criteria, such as those discussed above, band 250C may be determined to be the top band of head 256, corresponding to head top 256A, and position 256B the center of the top of the head. Knowing the center of the top of the head, it may then be concluded that some other body parts, such as the torso and legs, are below the top of the head, when a person is interrogated in a standing position. Also, it may be concluded that subject 212 may be divided into first and second or left and right image subject sides 266 and 267 based on the location of the head, or more particularly, the center of the head. A vertical line, represented by dash-double-dot line 268, passing through head center 256B may separate sides 266 and 267.

It is seen that the methods just described identify a portion of the body, in particular the head, top of the head, or the center of the top of the head. Similar methods and criteria may be used to determine other portions of the body, such as the torso, legs, bottom of the feet, and the like. An additional feature of the image may then be determined based at least partially on the identified portion of the body. For example, the orientation or pose of the body, or another body portion may be determined from the image, once it is known where the head or top of the head is positioned.

FIGS. 17-22 illustrate a method of imaging a subject including interrogating the subject with electromagnetic radiation in a frequency range of about 100 MHz to about 2 THz; generating, from the interrogating, image data representative of first and second image portions, with each image portion being of at least a portion of the person's body; determining from the image data a given feature of the first image portion and the given feature of the second image portion, the given feature being related to the orientation of the person's body; and determining the orientation of the person's body from the given feature of the first image portion and the given feature of the second image portion.

During interrogating, a person may be positioned in different orientations. The orientation of the person or other subject may be useful in determining features of the image, such as determining where on an image of the person's body objects carried by the person may likely be positioned, or determining which portion or portions of the person's image are important for protecting the person's privacy concerns. Additionally, some interrogating apparatus may not be capable of providing images of the person from all orientations when the person is in a single position. Images from all orientations, though, may be provided by having the person stand in a plurality of orientations relative to the interrogating apparatus. For example, if an interrogating apparatus images a person's body along a limited arc, such as opposing 110-degree arcs, then portions of the person's body may not be imaged in a single scan. Imaging from more or all sides or orientations around the person may be provided by positioning the person in a first orientation for a first interrogating operation or scan, and then repeating the scan with the person in one or more additional orientations, such as a second orientation different than the first orientation. In this example, the person may be scanned while in a second orientation that is rotated 90 degrees relative to the first orientation.

Figure 17:
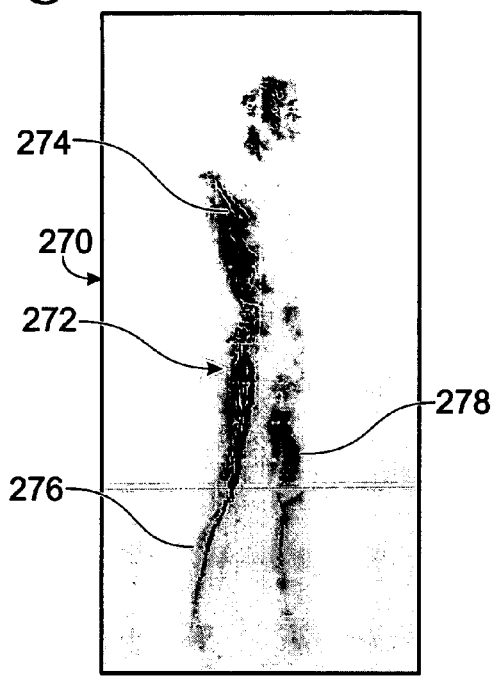
FIG. 17 is an image from an imaging system of FIG. 1 or FIG. 2, of a person in a first orientation.

FIG. 17 illustrates an image 270 of a subject 272 made from an imaging system 20, with a person's body 274 facing at an acute angle, such as 45 degrees, to the right relative to an observer or reference position. Image 270 may represent for each pixel or (x,y) coordinate, the highest response from a series of depth or distance measurements from the antenna array 34 to the subject 28. The depth measurements thus may represent image values in the z-direction, which direction is normal to the plane of image 270. The depth is represented on the image as a level of intensity, the areas of the subject that are closer to a reference, such as the antenna array or an observer, are darker in this example, thereby giving the image a three-dimensional or shaded effect. In this image it is seen that the person's right leg 276 is closer to the observer or reference than the left leg 178.

Figure 18:
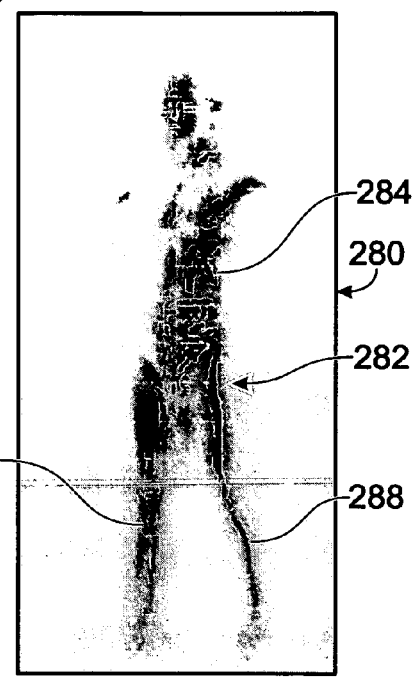
FIG. 18 is an image from an imaging system of FIG. 1 or FIG. 2, of a person in a second orientation.

FIG. 18 is similar to FIG. 17. In FIG. 18, an image 280 includes a subject 282 that includes a person's body 284 with right and left legs 286 and 288, respectively. In this image, body 284 is facing at an acute angle, such as 45 degrees, to the left. With the body in this pose, the right leg is closer to the antenna-array reference than the left leg.

Figure 19:
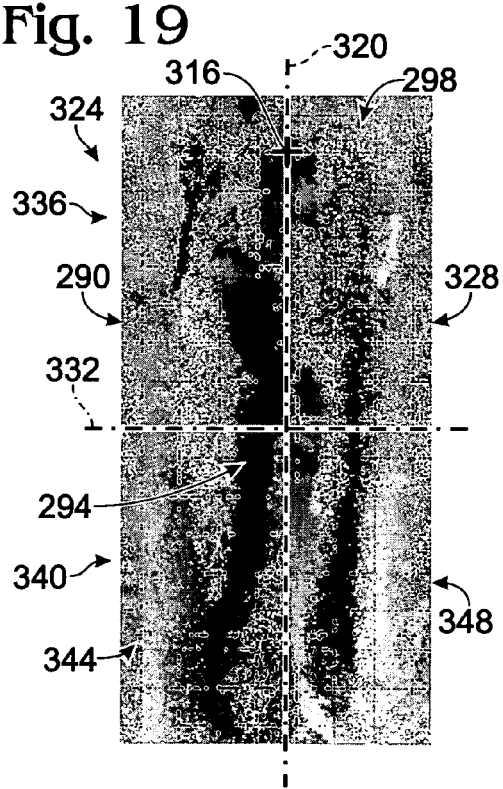
FIG. 19 is an image of relative detected distance from a reference for the person in the first orientation.
Figure 20:
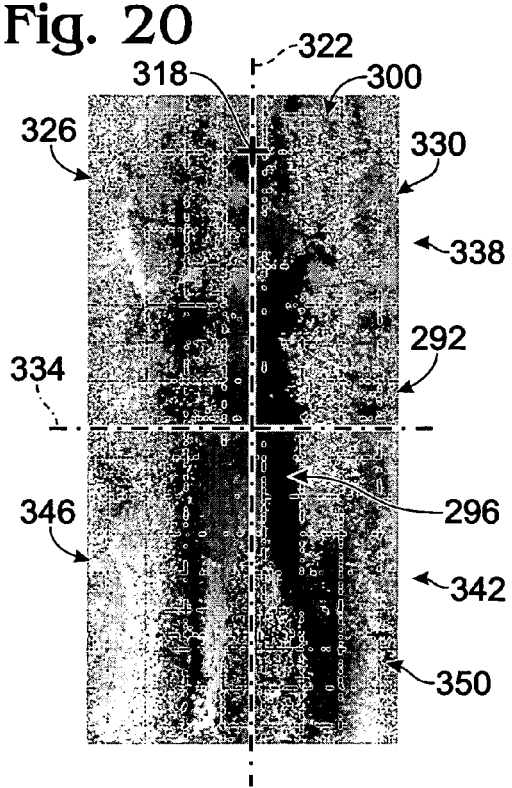
FIG. 20 is an image of relative detected distance from the reference for the person in the second orientation.
Figure 21:
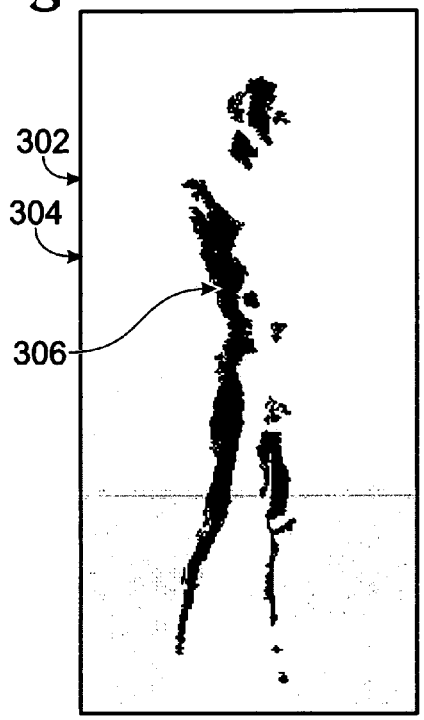
FIG. 21 is an image derived by applying an intensity threshold to the image of FIG. 17.
Figure 22:
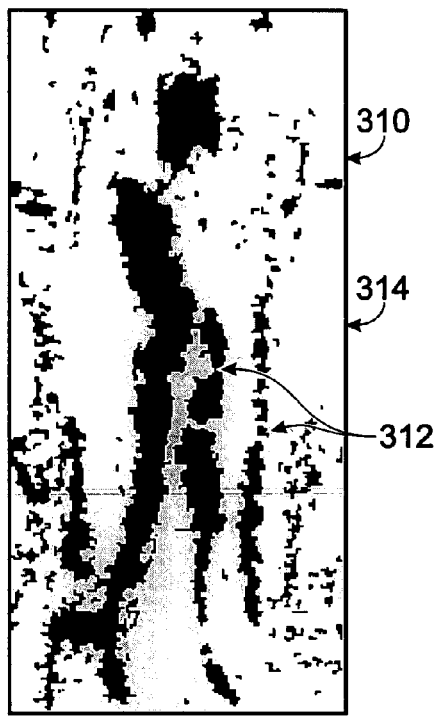
FIG. 22 is an image derived by applying a distance-variation threshold to the image of FIG. 19.

FIGS. 19 and 20 include respective images 290 and 292 of relative depth or distance values for pixels in images 270 and 280, respectively. The darker the pixel, the shorter the distance to the reference. It is seen that the imaging system used may produce relatively consistent depth values for the respective subjects 294 and 296, whereas respective background areas 298 and 300 may be generally mottled, inconsistent, or have higher depth variance.

One or both of the images of FIGS. 17 and 18, and FIGS. 19 and 20 may be further processed in order to limit the amount of depth data, represented by FIGS. 19 and 20, that is considered in determining the orientation of the subject(s) in one or both of FIGS. 17 and 18. For example, a threshold may be applied to FIGS. 17 and 18 to produce a high contrast mask or image that may facilitate distinguishing between the background and the subject. When such a threshold is applied to image 270, for instance, a black and white image 302, shown in FIG. 21, may be produced. This image may be produced by assigning a first value, such as the value for black, to any pixel with an intensity level below a threshold. Correspondingly, a second value that may be distinctive from the first value, such as a value corresponding to white, may then be applied to any pixel with an intensity level above the threshold. The background 304 is shown in the image as a white region, whereas the subject 306 is shown as black regions.

Differences in the character of the subject and background in depth images 290 and 292 of FIGS. 19 and 20 also may be used to distinguish the subject from the background. This may be accomplished by applying an m×n window, such as a 3×3 window, over each of the pixels in depth images 290 and 292. For each position of the window, a range of depth values of the pixels in the window may be determined. If the range of values is low enough to be below a threshold value, indicating a corresponding level of consistency of the depth values, the selected pixel may be assigned a first value, such as a value for black. Correspondingly, if the range of values is high enough to be above the threshold value, the selected pixel may be assigned a second value that is distinctive from the first value, such as a value for white, indicating greater inconsistency in the depth values. Applying this technique to image 290 of FIG. 19, a mask image 310 shown in FIG. 22 may be produced. Anomalies in depth image 290 are seen to produce, in this case, scattered black "subject" regions 312 on a white "background" region 314.

The depth data illustrated in FIGS. 19 and 20 may then be divided into sub-regions for depth differential analysis. Various approaches may be used to divide the data. One approach is to determine the tops 316 and 318 of the heads of the subjects 304 and 312, respectively, as previously described with reference to FIGS. 4-16. Vertical dividing lines 320 and 322 passing through the tops of the heads may then divide the subjects into respective left halves 324 and 326, and right halves 328 and 330. Horizontal lines 332 and 334, similarly may divide the subjects into top halves 336 and 338, and bottom halves 340 and 342. The result is that lower left quadrants 344 and 346, and lower right quadrants 348 and 350 are defined. It is seen that in both images, for the orientations used, the right leg is substantially in the lower left quadrant and the left leg is substantially in the lower right quadrant. Different subject orientations or positions and different ways of dividing the image may produce different results.

The image data in the different sub-regions may be analyzed individually or collectively. That is, the image in a single sub-region may be analyzed, different sub-regions in the same image may be analyzed, or the same or different sub-regions in different images may be analyzed. In this example, the lower left quadrant of one image may be compared to the lower right quadrant of the same image, the lower right (or left) quadrant of one image may be compared to the lower right (or left) quadrant of another image, or a combination of the two. Optionally or additionally, a plurality of sub-regions on a plurality of images may be compared. These techniques may also be applied where it is desired to determine the orientation of a subject relative to a reference for one or more of a plurality of different scans around a subject. Where the relative scan orientations are known, by identifying an orientation of the person in one of the scans, the orientations of the person in the other scans may then be computed.

Depth data for only a portion of the pixels in a sub-region may be used. In the present example, data for pixels that have a black value for both intensity-threshold image 302 and depth-variability threshold image 310 may be used. For each of the two lower quadrants for each image, the depth values for all of the selected pixels may be summed. The sum may then be divided by the number of selected pixels to get an average pixel value for the quadrant. Thus, an average pixel value may be determined for both the lower left quadrant and the lower right quadrant.

A depth differential may be determined by subtracting the average pixel value for one quadrant from the average pixel value for the other quadrant. For example, the average pixel value for the lower left quadrant may be subtracted from the average pixel value for the lower right quadrant. For the right-facing pose of image 270 of FIG. 17, the left leg, predominantly appearing in the lower right quadrant, is further away than the right leg, which predominantly appears in the lower left quadrant. As a result, the average depth value for the lower right quadrant may be less than the average depth value for the lower left quadrant. The depth differential may accordingly be negative in this case.

The reverse may be true of image 280 for the left-facing subject of FIG. 18. In this image, the left leg, predominantly appearing in the lower right quadrant, is closer than the right leg, which appears predominantly in the lower left quadrant. With the average depth value of the lower right quadrant greater than the average depth value of the lower left quadrant, the depth differential for image 280 may be a positive value.

In this example, a determination may be made as to which of two possible poses or orientations the subject is in. The determination may be based on the sign of the depth differential. That is, a positive depth differential indicates the subject is in a left-facing orientation and a negative depth differential indicates the subject is in a right-facing orientation. In this case, the threshold for comparison is zero. The combination of the results of the two poses may also be used in a determination. For example, if one of the depth differential values is near zero, then a greater absolute value for the other depth differentials may be used for determining the orientations of both images.

Additionally, if there are potentially other poses that may exist, or that may be identified, then a threshold other than zero may be used for comparison. For example, in one of the poses, the left and right quadrants of the subject image may be generally balanced, such as when the subject is facing directly toward or away from the reference or is facing fully to the left or to the right with both feet together. In such a case, the depth differential for the balanced image may average zero but typically have a depth differential with a value in a suitable range of values, such as plus or minus a threshold value, such as one fourth, one third, or one half of a maximum depth value.

It will be appreciated that one or more other sub-regions may be used for comparison or other analysis. For instance, the left and right sides of the torso area, a fraction of the torso area, and/or left and right sides of the entire subject area may be used.

The above techniques describe exemplary ways for locating a part of the subject's body, such as the top of the head, and also determining the orientation of the subject relative to a reference perceived as the viewer in the images provided. Such techniques may be useful for further image processing, such as determining a characteristic of the image as represented by image data, or for altering an image. An example of this latter function may be for alleviating privacy concerns of persons being surveilled. An example of a further method of surveilling a subject including a person's body may thus include interrogating the subject with electromagnetic radiation in a frequency range of about 100 MHz to about 2 THz; generating, from the interrogating, image data representative of at least a first image of the person's body; determining from the image data the location in the image of a first portion of the person's body; and replacing the first portion of the person's body with a substitute image portion.

Figure 23:
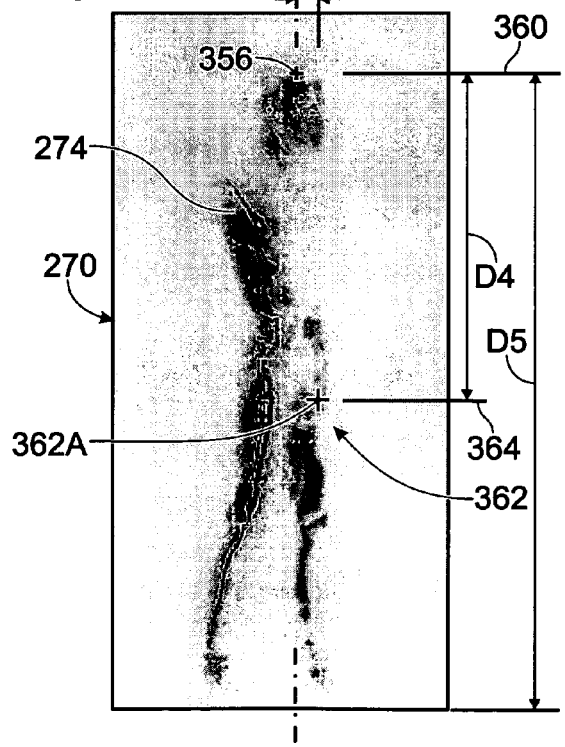
FIG. 23 is a copy of the image of FIG. 17.
Figure 24:
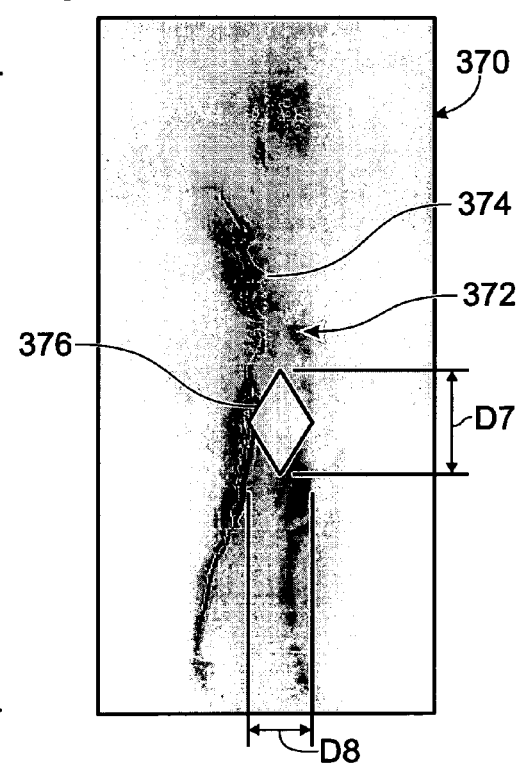
FIG. 24 is a modified version of the image of FIG. 23.

FIGS. 23 and 24 illustrate an example of a method of replacing a portion of an image with a substitute image portion to protect concerns about the privacy of certain parts of the person's body. FIG. 23 is a duplicate of image 270 shown in FIG. 17. A center of the top of the head 356 corresponds to the intersection of vertical line 358 and a horizontal line 360. Using the subject orientation analysis described with reference to FIGS. 17-22, the orientation of the surveilled person's image may be determined to be facing forward and to the right in the image. The orientation may be determined from each scanned image, or may be based on a known rotation or other movement of the interrogating apparatus relative to a base or reference image. For instance there may be a known number of frames or images of a subject, each being at a different rotational perspective or angle. A look-up table may be used to indicate whether the image requires hiding of a privacy region based on the orientation of the subject in the current image.

Once this information is known about the subject, then a portion 362 of the subject image, also referred to as a privacy region, may be determined based on typical or expected body proportions for people. For example, the lower torso area of a person may be determined to be a particular proportion of the distance between the top of a person's head and the bottom of the feet, when the person is standing upright. Specifically, image portion 362 may be located a distance, represented by distance D4, that is a fraction of the total height of a person, represented by distance D5. Thus, as a specific example, the privacy portion may be determined to be located at a level corresponding to the fraction D4/D5 of the distance D5 from the top of the head centered along a horizontal line 364. This fraction may be about one half in some examples, or in other examples about 54 percent of the length D5 from the top of the head.

Further, when the orientation of a surveilled person is not directly facing toward or away from the image observer reference, the privacy area may be offset horizontally from centerline 358. In the orientation shown in FIG. 23, a center 362A of the privacy image portion 362 may be offset a horizontal distance D6 from the centerline. Distance D6 may be determined empirically, a standard offset may be used, or no offset may be used.

Once a position represented by center 362A is determined, then a portion of image 270 may be replaced with a substitute image portion. An example of such a modified image 370 is illustrated in FIG. 24. Image 370 may include a subject 372, of a person's body 374. A portion of the person's body may be replaced with a substitute image 376.

Substitute image 376 may have any shape, pattern, design, configuration and/or image considered appropriate or suitable. Image 376 in this example has a diamond shape with a uniform color or intensity, and has a height D7 and a width D8. An image of a privacy area may also be replaced with a modified image of the privacy area, such as an image modified as described above with reference to FIG. 5 so that the image is no longer clear.

Substitute image 376 may have a fixed size or the size may be variable. In this example, the height D7 may be 0.16 times the height of the surveilled person. The width D8 may correspond to the width of 35 pixels. The width of substitute image 376 also may be made variable. For example, the width may depend on the angle of the person to the observer reference, with a side view having a smaller width than a more direct front or back view.

Modified image 370 may provide an image with the privacy portion replaced with a substitute image. The substitute image may be shaped and sized to provide for coverage of as much of the original image as considered appropriate. Further, multiple substitute images may be used. This approach leaves a large majority of the original image available for viewing by an operator of the imaging system or other appropriate personnel. In this way, the observer of the image may check or supplement results of any automatic detection of objects on a surveilled person.

FIGS. 25-36 illustrate further examples of privacy subject imaging in which a privacy image portion may be replaced with a modified image portion. As a first example, FIGS. 25-30 illustrate a method of modifying a portion of a subject image to provide a level of privacy for the imaged subject. As with the previous images, the images contained in these figures represent computer data, and are shown in a reverse or negative intensity format to render the images lighter and therefore more satisfactorily reproducible by digital equipment. The procedures involved do not necessarily require that the data be depicted or even be capable of depiction or display as a pictorial or other visually identifiable image. Rather, the images illustrate or represent characteristics or features of the subject data, and are intended to facilitate an understanding of the procedures involved.

Figure 25:
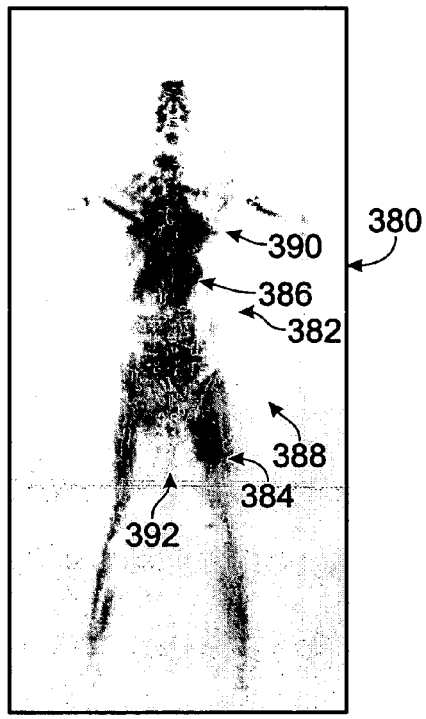
FIG. 25 is a reversed representative image from an imaging system of FIG. 1 or FIG. 2 of a subject including the front of a person.

In particular, FIG. 25 depicts a full original or input image 380 generated from an interrogation of a subject. Image 380 includes a subject 382 in the form of a person having a body 384 with a torso 386. A background 388 may surround the subject. Certain regions or portions of the subject 382 may be the subject of privacy concerns of the person imaged, such as an upper privacy region 390 located in the region of the upper torso or a lower privacy region 392 located at the base of the torso.

As mentioned above, a privacy region may be masked by replacing a portion of the image in or associated with the privacy region with a substitute image, which may be a portion of the original image that has been modified. Initially, a determination may be made as to the location of the privacy region. This may include determining the location of the top of the head, as was described with reference to FIGS. 4-16.

Then a determination may be made as to the initial pose of the person, as was described with reference to FIGS. 17-22. The orientation of the subject in the present image may then be determined based on the relative orientation of the subject relative to the initial pose. Once the pose and orientation of the subject are known, then a determination may be made as to whether a privacy region is to be hidden, and if so, the location of the privacy region, as was discussed with reference to FIGS. 23 and 24.

Figure 26:
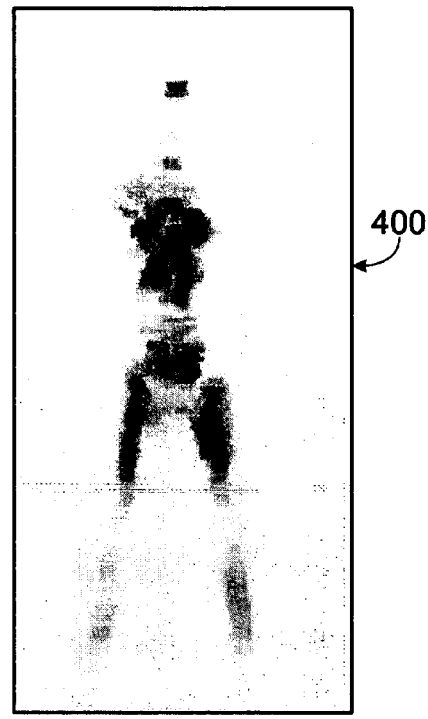
FIG. 26 is a modified image derived from the image of FIG. 25.
Figure 27:
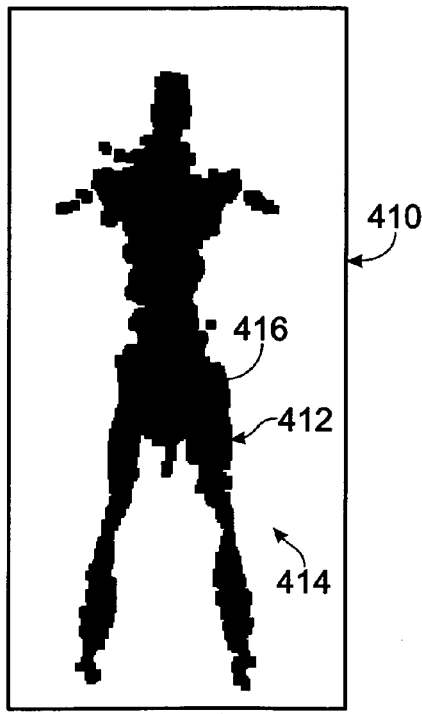
FIG. 27 is a body mask derived from the image of FIG. 25.

Image 370 of FIG. 24 shows an example of replacing a privacy region image with an arbitrary substitute image. In some examples, the original image may be modified by morphing the original image, such as image 380. Although an image may be morphed in many different ways, one way is to morph it is as was performed on image 110 of FIG. 4 to produce image 120 of FIG. 5. An example of a morphed image 400 produced from image 380 using a similar method, but with parameters changed as considered appropriate to address privacy concerns, is illustrated in FIG. 26.

Figure 5:
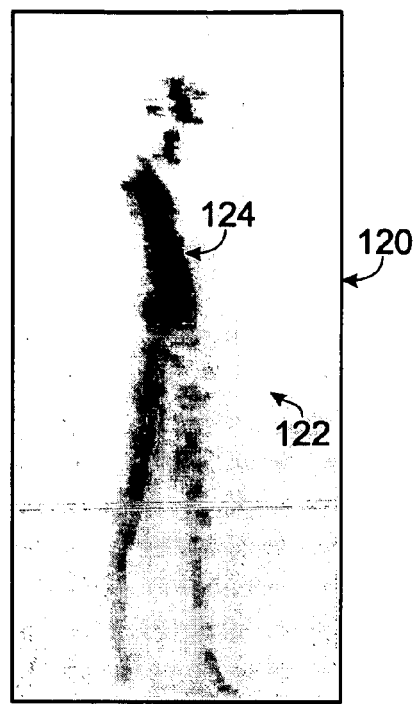
FIG. 5 is a modified image derived from the image of FIG. 4.
Figure 6:
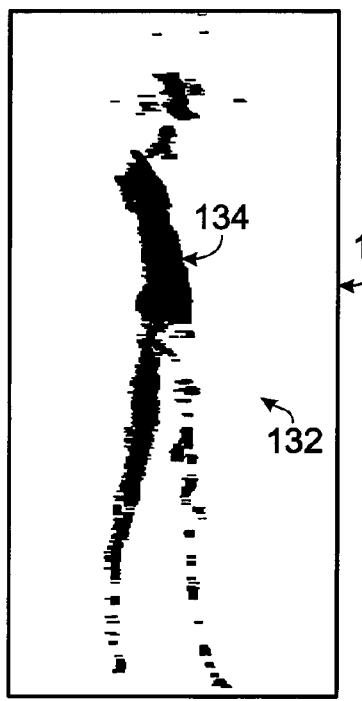
FIG. 6 is a further modified image derived from the image of FIG. 5.

In this example, a mask of the body of the subject may be made for use in determining the location of the privacy region, similar to the methods described with reference to FIG. 5, using the same or different steps and/or parameters for the steps, such as the size of windows used to dilate or erode an image. Accordingly, a threshold image may be produced, such as image 410 including a subject 412 and a background 414 shown in FIG. 27. Subject 412 may also be referred to as a body mask 416.

Figure 28:
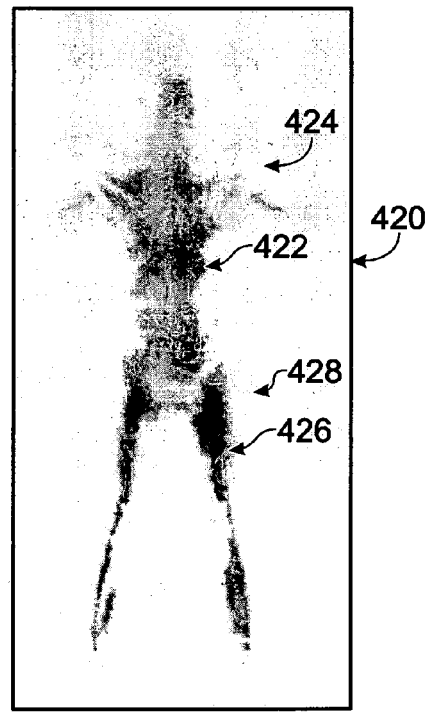
FIG. 28 is a modified image derived from the combination of the images of FIGS. 25 and 26.

Using images 380, 400 and 410, a composite privacy image 420, shown in FIG. 28, may be produced. Image 420 may include a subject 422 that includes an unmodified original image portion 424 and a modified privacy image portion 426. In this example, the privacy image portion is located in the vicinity of a lower privacy region 428. This privacy image portion 426 has a generally circular configuration. Any suitable configuration may be used, such as regular or irregular forms that may be oval, polygonal, oblong, simple, compound or convoluted.

Figure 29:
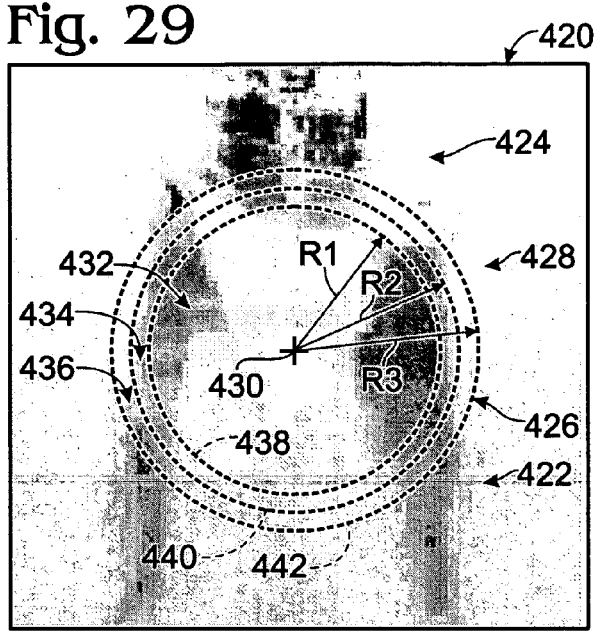
FIG. 29 is an enlarged portion of the image of FIG. 28.

FIG. 29 is an enlarged view of the privacy region 428 and surrounding portions of the unmodified image portion 424 of image 420. A center 430 of the privacy region 428, determined as described with reference to FIGS. 23 and 24, may be used as a point of reference for generating and positioning privacy image portion 426.

Privacy image portion 426 may be a single substitute image portion, as shown in FIG. 24, or it may be made of a collection or combination of overlapping or nonoverlapping image portions. In this example, privacy image portion 426 is divided into three subregions 432, 434 and 436. Subregion 432 is an inner subregion and includes the portion of region 428 within an inner circle 438 centered about center 430 and having a radius R1. Subregion 434 is an intermediate subregion and includes the portion between inner circle 438 and an intermediate circle 440. Intermediate circle 440 has a radius R2. Similarly, subregion 436 is an outer subregion and includes the portion of region 428 between intermediate circle 440 and an outer circle 442. Outer circle 442 has a radius R3.

The sizes and configuration of any subregions used may be selected to fit particular imaging applications. In this example, the radii are determined based at least in part on the body height of the subject. For example, radii R1, R2 and R3 may respectively be set to equal 0.08, 0.09, and 0.095 times the height of an imaged person. As a further example, then, for a subject having an image height of 348 pixels, the radii R1, R2 and R3 may be set to 28, 31 and 33 pixels, respectively. This approach provides that the size of the privacy image region changes is proportional to the size of the imaged subject.

Different images may be placed in different subregions to form a composite privacy image portion 426. In this example, the values of corresponding pixels from morphed image 400 are used in inner subregion 432. In intermediate subregion 434, the values of corresponding pixels from morphed image 400 are used so long as the pixel is also included in the body mask 412 of image 410. Otherwise, corresponding values of pixels from original image 380 are used.

Figure 30:
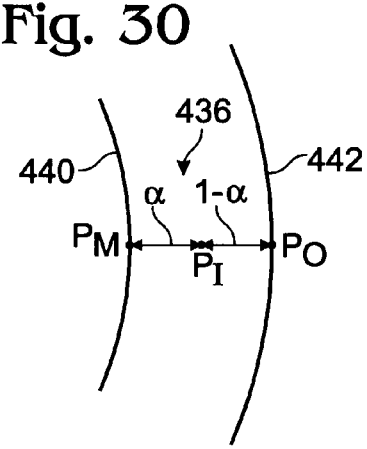
FIG. 30 is an illustration of steps used to combine portions of the images of FIGS. 25 and 26.
Figure 31:
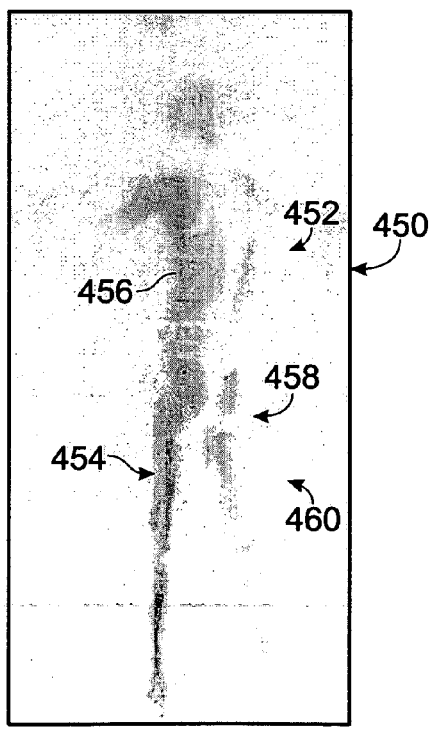
FIG. 31 is a reversed representative image from an imaging system of FIG. 1 or FIG. 2 of a subject including the back of a person.

In outer subregion 436, values for pixels that are not on the body mask 412 are set equal to those of corresponding pixels from original image 380. Values for pixels that are on the body mask are produced by merging or blending pixel values from images 380 and 400. The proportion of blending depends on the relative position of a pixel between circles 440 and 442. An example of this is illustrated in FIG. 30, which shows representative portions of circles 440 and 442. A location $P_I$ of a pixel in outer subregion 436 is at an intermediate point between a point $P_M$ on the intermediate circle having a morphed pixel value, and a point $P_O$ on the outer circle, having an original pixel value.

For $0<\alpha<1$, the value of $P_I = \alpha P_M + (1-\alpha) P_O$. Thus, the contribution of the morphed pixel value varies from 100 percent on intermediate circle 440 to none on outer circle 442, and conversely the contribution of the original pixel value varies from none on intermediate circle 440 to 100 percent on outer circle 442. As a result, the image of the outer subregion varies gradually from the morphed image at the intermediate circle to the original image at the outer circle. Accordingly, features of the original image are more apparent adjacent the outer circle than adjacent the inner circle. This produces a smooth visual transition between the morphed image and the original image.

Additionally, since the morphed image is produced from the original image, it also contains characteristics of the original image that may help identify objects in the privacy region. An object may produce a morphed image that appears differently than a morphed image of a person's body. An image contained within the diamond shape of the substitute image 376 shown in FIG. 24, may not contain original image information if it is not derived from the original image.

An procedure similar to the procedure described with reference to FIGS. 31-36, may be used for producing a privacy image of the back of a person. An original image 450, shown in FIG. 31, may include a subject 452, with a body 454 having a torso 456 and a lower torso area 458, and a background 460 generally surrounding the subject.

Figure 32:
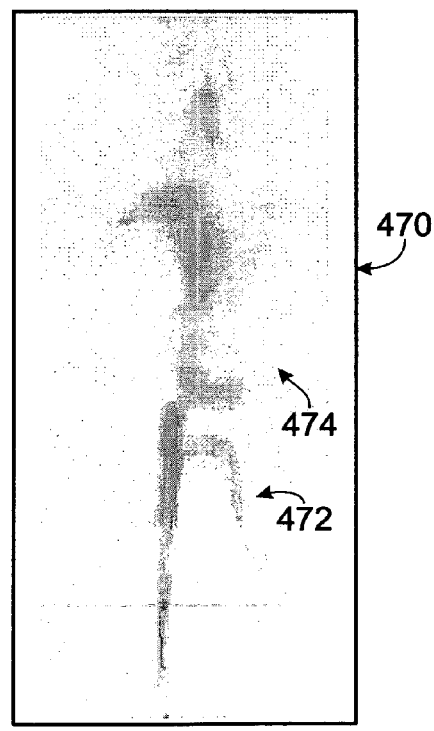
FIG. 32 is a modified image derived from the image of FIG. 31.

A morphed image 470, shown in FIG. 32, including a subject 472 and a background 474 may be produced from original image 450. Morphed image 400 was produced by eroding the original image, and then dilating the eroded image. It has been found that a desirable objective in producing a rear privacy image is to eliminate any image of a generally vertically extending separation in the lower torso area. This may be achieved, at least in part by first dilating the original image, and then eroding it. The subject may be dilated by selecting high pixel values in horizontally elongate windows of a selected size or sizes to replace the original pixel values. This tends to enlarge the image. It may then be eroded, or reduced in size by reversing the process. Further processing may also be used, such as vertically and/or horizontally smoothing the eroded image.

Figure 14:
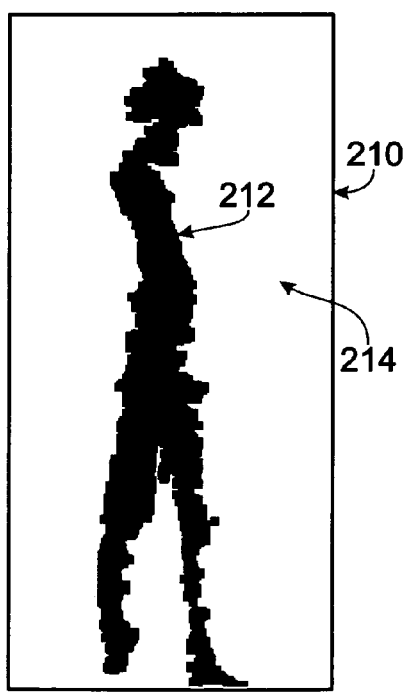
FIG. 14 is a body mask derived from the image of FIG. 13.
Figure 33:
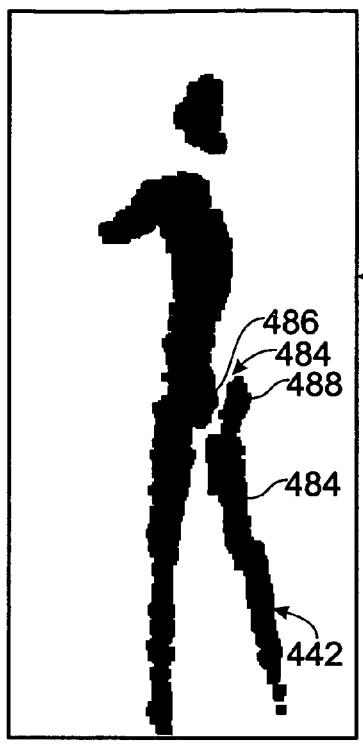
FIG. 33 is a body mask derived from the image of FIG. 31.

A threshold-based image 480 shown in FIG. 33 may also be produced from the original image, as has been described for producing body mask image 210 shown in FIG. 14. Image 480 may include a subject 482 that may be used as a body mask 484. It is seen that subject 482 includes a separation 485 between buttocks 486 and 488. This separation may be substantially eliminated by further processing image 480. For example, the image may be dilated using a sufficiently horizontally extending window, such as a window that is 15 pixels wide by 3 pixels high. This will tend to eliminate the separation and fill in holes in the subject. The image may then be eroded by applying a suitable window, such as a vertically long window, such as a 1-pixel wide by 11-pixel high window. This latter erosion tends to reduce the size of the body mask as well as form vertically elongate elements in the image, further obscuring the rear separation.

Figure 34:
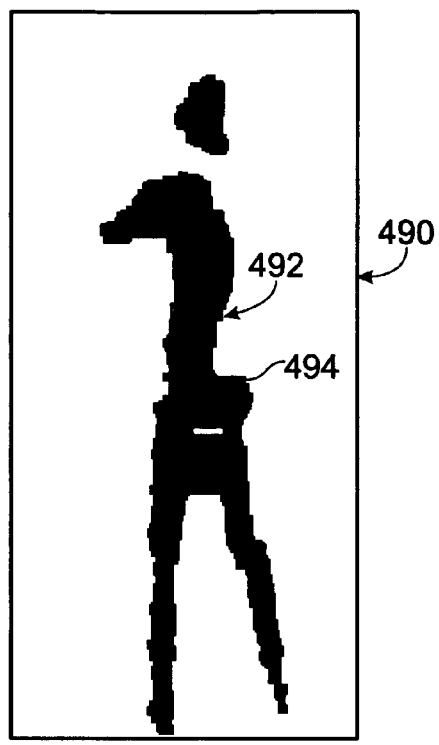
FIG. 34 is body mask derived from the body mask of FIG. 33.

A result of such a process is a modified image 490, shown in FIG. 34, which image includes a subject 492 forming a body mask 494. It is seen that the separation that existed in body mask 484 has been eliminated and the lower torso area generally well filled in. Further processing may also be performed on this image, as appropriate, such as further dilating, eroding, or smoothing, such as with a low-pass Gaussian or other function or filter.

Figure 35:
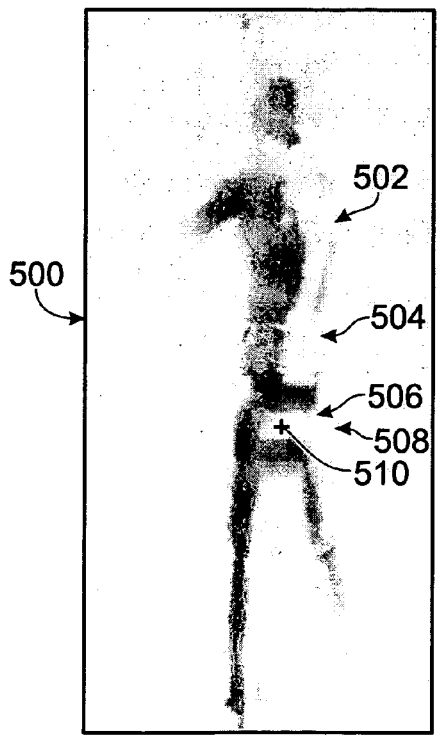
FIG. 35 is a modified image derived from the combination of the images of FIGS. 31 and 32.

Using images 450, 470 and 490, a composite privacy image 500, shown in FIG. 35, may be produced. Image 500 may include a subject 502 that includes an unmodified original image portion 504 and a modified privacy image portion 506. The privacy image portion is located in the vicinity of a lower privacy region 508 in this example.

Figure 36:
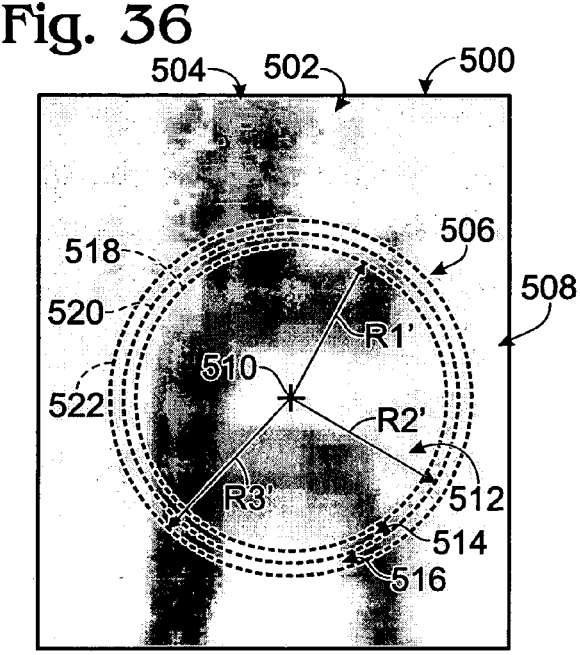
FIG. 36 is an enlarged portion of the image of FIG. 35.

Privacy image portion 506 was produced in a manner like that described above to produce privacy image portion 426 of privacy image 420. FIG. 36 is an enlarged view of the privacy region 508 and surrounding portions of the unmodified image portion 504 of image 500. In this example, privacy region 508 has a center 510, determined as described with reference to FIGS. 23 and 24. Privacy image portion 506 is divided into three subregions 512, 514 and 516 bounded by respective circles 518, 520 and 522. As with privacy image portion 428, these circles have respective radii R1, R2 and R3 of increasing length. These radii may be different or the same for subjects positioned in different orientations or for different subjects. The pixel values used for the three subregions may be determined in the same way as was described with reference to privacy image portion 428. It will be appreciated that the image portions for part or all of one or more of the subregions may be replaced with images of objects identified by an operator or identified automatically from the original input image data.

While embodiments of imaging systems and methods of imaging have been particularly shown and described, many variations may be made therein. This disclosure may include one or more independent or interdependent inventions directed to various combinations of features, functions, elements and/or properties, one or more of which may be defined in the following claims. Other combinations and sub-combinations of features, functions, elements and/or properties may be claimed later in this or a related application. Such variations, whether they are directed to different combinations or directed to the same combinations, whether different, broader, narrower or equal in scope, are also regarded as included within the subject matter of the present disclosure. An appreciation of the availability or significance of claims not presently claimed may not be presently realized. Accordingly, the foregoing embodiments are illustrative, and no single feature or element, or combination thereof, is essential to all possible combinations that may be claimed in this or later applications. The claims, accordingly, define inventions disclosed in the foregoing disclosure, but any one claim does not necessarily encompass all features or combinations that may be claimed. Where the claims recite "a" or "a first" element or the equivalent thereof, such claims include one or more such elements, neither requiring nor excluding two or more such elements. Further, ordinal indicators, such as first, second or third, for identified elements are used to distinguish between the elements, and do not indicate a required or limited number of such elements, and do not indicate a particular position or order of such elements unless otherwise specifically stated.

INDUSTRIAL APPLICABILITY

The methods and apparatus described in the present disclosure are applicable to security, monitoring and other industries in which surveillance or imaging systems are utilized.

The invention claimed is:

1. A method of surveilling a subject including a person's body comprising:
   interrogating the subject with electromagnetic radiation in a frequency range of about 100 MHz to about 2 THz;
   generating, from the interrogating, image data representative of at least a first image of a surface of the person's body;
   determining, via a processor, the location in the image corresponding to a first given portion of the surface of the person's body from the image data;
   determining a region of the image defined by a boundary surrounding and extending beyond the location in the image corresponding to the first given portion of the surface of the person's body; and
   replacing the region of the image corresponding to the first given portion of the surface of the person's body with a substitute image portion.

2. The method of claim 1, in which the first given portion of the surface of the body is the lower end of the trunk.

3. The method of claim 1, in which replacing the first region of the image includes replacing the first portion of the image with a substitute image portion having a variable size.

4. The method of claim 3, the method further comprising determining a size of the substitute image portion based at least in part on a dimension of the person's body.

5. The method of claim 1, in which determining the location in the image corresponding to a first given portion of the surface of the person's body includes determining the location in the image corresponding to a second given portion of the person's body, and determining the location in the image corresponding to the first given portion of the surface of the person's body based, at least in part, on the identified location in the image corresponding to the second given portion of the person's body.

6. The method of claim 5, in which determining the location of a second portion of the body includes determining the location of the head.

7. The method of claim 5, in which determining the location of a second portion of the body includes determining the location of a boundary of the body.

8. The method of claim 7, in which determining the location of a second portion of the body includes determining the location of the top of the head.

9. The method of claim 8, in which determining the location of the top of the head includes distinguishing image data corresponding to the subject from image data corresponding to a background of the subject.

10. The method of claim 9, in which generating image data includes generating image data corresponding to the subject having picture elements generally having a first feature and image data corresponding to the background having picture elements generally having a second feature different than the first feature, and distinguishing image data includes identifying picture elements having the first feature.

11. The method of claim 5, in which determining the location in the image corresponding to a first given portion of the surface of the person's body includes determining the orientation of the person's body.

12. The method of claim 11, in which generating image data includes generating image data of a first image of the person's body in a first orientation and a second image of the person's body in a second orientation, and determining the orientation of the person's body includes comparing (a) a first portion of the first image corresponding to a third given portion of the person's body in the first orientation with (b) a first portion of the second image corresponding to the third given portion of the person's body in the second orientation.

13. The method of claim 12, in which generating image data includes generating image data representative of a relative distance of the person's body from a reference position, and determining the orientation of the person's body includes determining the relative distance from the reference position of at least a fourth given portion of the person's body represented by a second portion of the first image compared to one or both of (a) a fifth given portion of the person's body represented by a second portion of the second image, and (b) a sixth given portion of the person's body represented by a third portion of the first image.

14. The method of claim 11, in which generating image data includes generating image data of a first image of the person's body representative of a relative distance of the person's body from a reference position, and determining the orientation of the person's body includes determining the relative distance from the reference position of at least a third given portion of the person's body represented by a first portion of the first image compared to a fourth given portion of the person's body represented by a second portion of the first image.

15. The method of claim 11, in which generating image data includes generating image data corresponding to a three-dimensional holographic first image of at least a third given portion of the person's body.

16. The method of claim 1, in which generating image data includes generating image data corresponding to a three-dimensional holographic first image of at least a second given portion of the person's body.

17. An imaging system comprising:
an antenna assembly including at least a first antenna apparatus, each antenna apparatus configured to transmit toward and receive from a subject, including a person and any discernable objects with the person, in a subject position, electromagnetic radiation in a frequency range of about 100 MHz to about 2 THz, from positions spaced from the subject position, the antenna assembly producing an image signal representative of the received radiation; and
a controller adapted to produce from at least a portion of the image signal image data representative of at least a first image of a surface of the person's body, to determine from the image data the location in the image corresponding to a first given portion of the surface of the person's body, determining a region of the image defined by a boundary surrounding and extending beyond the location in the image corresponding to the first given portion of the surface of the person's body; and to replace the region of the image corresponding to the first given portion of the surface of the person's body with a substitute image portion.

18. The system of claim 17, in which the first given portion of the surface of the body is the lower end of the trunk.

19. The system of claim 17, in which the controller is further adapted to replace the region of the image corresponding to the first given portion of the surface of the person's body with a substitute image portion having a variable size.

20. The system of claim 19 in which the controller is further adapted to determine a size of the substitute image portion based at least in part on a dimension of the person's body.

21. The system of claim 17, in which the controller is further adapted to determine the location in the image corresponding to a second given portion of the person's body, and to determine the location in the image corresponding to the first given portion of the surface of the person's body based, at least in part, on the identified location in the image corresponding to the second given portion.

22. The system of claim 21, in which the controller is further adapted to determine the location of the head as the second portion.

23. The system of claim 21, in which the controller is further adapted to determine the location of a boundary of the body.

24. The system of claim 23, in which the controller is further adapted to determine the location of the top of the head.

25. The system of claim 24, in which the controller is further adapted to distinguish image data corresponding to the subject from image data corresponding to a background of the subject.

26. The system of claim 25, in which the controller is further adapted to generate image data corresponding to the subject having picture elements generally having a first feature and image data corresponding to the background having picture elements generally having a second feature different than the first feature, and distinguishing image data includes identifying picture elements having the first feature.

27. The system of claim 21, in which the controller is further adapted to determine the orientation of the person's body.

28. The system of claim 27, in which the controller is further adapted to generate image data of a first image of the person's body in a first orientation and a second image of the person's body in a second orientation, and to compare (a) a first portion of the first image corresponding to a third given portion of the person's body in the first orientation with (b) a first portion of the second image corresponding to the third given portion of the person's body in the second orientation.

29. The system of claim 28, in which the controller is further adapted to generate image data representative of a relative distance of the person's body from a reference position, and to determine the relative distance from the reference position of at least a fourth given portion of the person's body represented by a second portion of the first image compared to one or both of (a) a fifth given portion of the person's body represented by a second portion of the second image, and (b) a sixth given portion of the person's body represented by a third portion of the first image.

30. The system of claim 27, in which the controller is further adapted to generate image data of a first image of the person's body representative of a relative distance of the person's body from a reference position, and to determine the relative distance from the reference position of at least a third given portion of the person's body represented by a first portion of the first image compared to a fourth given portion of the person's body represented by a second portion of the first image.

31. The system of claim 27, in which the controller is further adapted to produce image data corresponding to a three-dimensional holographic first image of at least a third given portion of the person's body.

32. The system of claim 17, in which the controller is further adapted to produce image data corresponding to a three-dimensional holographic first image of at least a third given portion of the person's body.

33. One or more computer-readable storage media having embodied therein a program of commands adapted to be executed by a computer processor to:
receive an image signal generated in response to an interrogation of a subject, including a person and any objects carried by the person, with electromagnetic radiation in a range of about 100 MHz to about 2 THz;
generate, from the interrogating, image data representative at least a first image of a surface of the person's body;
determine from the image data the location in the image corresponding to a first given portion of the surface of the person's body;
determine a region of the image defined by a boundary surrounding and extending beyond the location in the image corresponding to the first given portion of the surface of the person's body; and
replace a first portion the region of the image corresponding to the first given portion of the surface of the person's body with a substitute image portion.

34. The media of claim 33, in which the first given portion of the body is the lower end of the trunk.

35. The media of claim 33, in which the program is further adapted to be executed to replace the region of the image with a substitute image portion having a variable size.

36. The media of claim 33, in which the program is further adapted to be executed to determine the location in the image corresponding to a second given portion of the person's body, and determining the location in the image corresponding to the first given portion based, at least in part, on the identified location in the image corresponding to the second given portion of the person's body.

37. The media of claim 36, in which the program is further adapted to be executed to determine the location of the top of the head.

38. The media of claim 36, in which the program is further adapted to be executed to determine the orientation of the person's body.

39. An imaging system comprising:
means for interrogating a subject, including a person's body, with electromagnetic radiation in a frequency range of about 100 MHz to about 2 THz;
means for generating, from the interrogating, image data representative of at least a first image of a surface of the person's body;
means for determining from the image data the location in the image corresponding to a first given portion of the surface of the person's body;
means for determining a region of the image defined by a boundary surrounding and extending beyond the location in the image corresponding to the first given portion of the surface of the person's body; and
means for replacing the region of the image corresponding to the first given portion of the surface of the person's body with a substitute image portion.

* * * * *